US007811771B2

(12) United States Patent
Verheijen et al.

(10) Patent No.: US 7,811,771 B2
(45) Date of Patent: Oct. 12, 2010

(54) METHOD FOR THE FUNCTIONAL DETERMINATION OF MANNAN-BINDING-LECTIN ASSOCIATED SERINE PROTEASES (MASPS) AND COMPLEXES THEREOF

(75) Inventors: Johan Hendrikus Verheijen, Berkel En Rodenrijs (NL); Jan Roeland Occo Hanemaaijer, Voorhout (NL); Natascha Alexandra Van Lent, Gorinchem (NL); Johannes Hendrikus Nicolaas Lindeman, Noordwijkerhout (NL); Mohamed Rahoef Daha, Leiderdorp (NL); Johanna Roos, Katwijk (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 275 days.

(21) Appl. No.: 11/793,851

(22) PCT Filed: Dec. 19, 2005

(86) PCT No.: PCT/NL2005/000874

§ 371 (c)(1),
(2), (4) Date: Feb. 1, 2008

(87) PCT Pub. No.: WO2006/068469

PCT Pub. Date: Jun. 29, 2006

(65) Prior Publication Data

US 2008/0286803 A1    Nov. 20, 2008

(30) Foreign Application Priority Data

Dec. 23, 2004  (EP) .................................. 04078507

(51) Int. Cl.
*G01N 33/53* (2006.01)
(52) U.S. Cl. .......................... 435/7.1; 436/507; 436/513
(58) Field of Classification Search ....................... None
See application file for complete search history.

(56) References Cited

U.S. PATENT DOCUMENTS

2005/0118603 A1* 6/2005 Chun et al. .................... 435/6

FOREIGN PATENT DOCUMENTS

NL   0691409   *  2/1996
NL   1443116   *  4/2004

* cited by examiner

*Primary Examiner*—Jacob Cheu
(74) *Attorney, Agent, or Firm*—Weingarten, Schurgin, Gagnebin & Lebovici LLP

(57) ABSTRACT

This invention relates to the field of determining, assaying or quantifying activity of components of the complement system. More particularly, the invention relates to methods for detecting the presence or level of activity in a sample of mannan-binding-lectin associated serine proteases (MASPs) or complexes of such proteases with lectins and to detection of the particular lectins themselves. Provided is a method for determining the activity of a MASP in a sample, comprising incubating the sample with a pro-urokinase comprising at its activation site the consensus sequence Arg/Leu/Gly-Yyy-Arg/Lys-Ile/Leu/Val-Zzz-Gly-Gly cleavable by a MASP, wherein Yyy can be any amino acid and Zzz is preferably an aliphatic amino acid, and determining proteolytic activation of said pro-urokinase.

21 Claims, 9 Drawing Sheets

Figure 1:
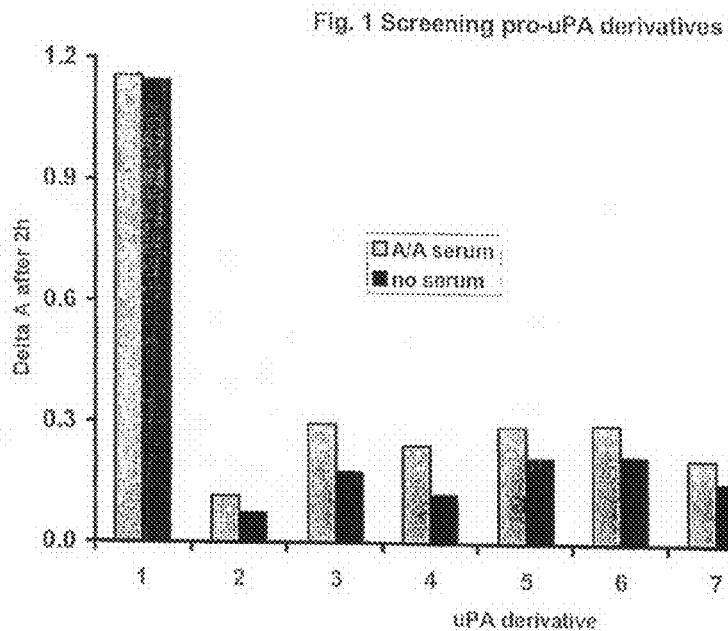

```
                              SEQUENCE LISTING

<160> NUMBER OF SEQ ID NOS: 30

<210> SEQ ID NO 1
<211> LENGTH: 7
<212> TYPE: PRT
<213> ORGANISM: Artificial
<220> FEATURE:
<223> OTHER INFORMATION: consensus sequence MASP activation site
<220> FEATURE:
<221> NAME/KEY: MISC_FEATURE
<222> LOCATION: (1)..(1)
<223> OTHER INFORMATION: Can be Arg, Leu or Gly
<220> FEATURE:
<221> NAME/KEY: misc_feature
<222> LOCATION: (2)..(2)
<223> OTHER INFORMATION: Can be any naturally occurring amino acid
<220> FEATURE:
<221> NAME/KEY: MISC_FEATURE
<222> LOCATION: (3)..(3)
<223> OTHER INFORMATION: Can be Arg or Lys
<220> FEATURE:
<221> NAME/KEY: MISC_FEATURE
<222> LOCATION: (4)..(4)
<223> OTHER INFORMATION: Can be Ile, Leu or Val
<220> FEATURE:
<221> NAME/KEY: VARIANT
<222> LOCATION: (5)..(5)
<223> OTHER INFORMATION: Can be any aliphatic amino acid

<400> SEQUENCE: 1

Xaa Xaa Xaa Xaa Xaa Gly Gly
1               5

<210> SEQ ID NO 2
<211> LENGTH: 8
<212> TYPE: PRT
<213> ORGANISM: Homo sapiens
```

```
<400> SEQUENCE: 2

Pro Arg Phe Lys Ile Ile Gly Gly
1               5

<210> SEQ ID NO 3
<211> LENGTH: 8
<212> TYPE: PRT
<213> ORGANISM: Artificial
<220> FEATURE:
<223> OTHER INFORMATION: activation site

<400> SEQUENCE: 3

Arg Gly Leu Arg Ile Ile Gly Gly
1               5

<210> SEQ ID NO 4
<211> LENGTH: 8
<212> TYPE: PRT
<213> ORGANISM: Artificial
<220> FEATURE:
<223> OTHER INFORMATION: activation site

<400> SEQUENCE: 4

Asn Leu Thr Arg Ile Val Gly Gly
1               5

<210> SEQ ID NO 5
<211> LENGTH: 8
<212> TYPE: PRT
<213> ORGANISM: Artificial
<220> FEATURE:
<223> OTHER INFORMATION: activation site

<400> SEQUENCE: 5

Ser Leu Gly Arg Ile Ile Gly Gly
1               5

<210> SEQ ID NO 6
<211> LENGTH: 8
<212> TYPE: PRT
<213> ORGANISM: Artificial
<220> FEATURE:
<223> OTHER INFORMATION: activation site

<400> SEQUENCE: 6

Ser Leu Gly Lys Ile Ile Gly Gly
1               5

<210> SEQ ID NO 7
<211> LENGTH: 8
<212> TYPE: PRT
<213> ORGANISM: Artificial
<220> FEATURE:
<223> OTHER INFORMATION: activation site

<400> SEQUENCE: 7

Gly Leu Gln Arg Ile Ile Gly Gly
1               5

<210> SEQ ID NO 8
<211> LENGTH: 8
<212> TYPE: PRT
<213> ORGANISM: Artificial
<220> FEATURE:
<223> OTHER INFORMATION: activation site

<400> SEQUENCE: 8
```

```
Gly Leu Gln Lys Ile Ile Gly Gly
1               5

<210> SEQ ID NO 9
<211> LENGTH: 8
<212> TYPE: PRT
<213> ORGANISM: Artificial
<220> FEATURE:
<223> OTHER INFORMATION: activation site

<400> SEQUENCE: 9

Gln Arg Gln Arg Ile Ile Gly Gly
1               5

<210> SEQ ID NO 10
<211> LENGTH: 8
<212> TYPE: PRT
<213> ORGANISM: Artificial
<220> FEATURE:
<223> OTHER INFORMATION: activation site

<400> SEQUENCE: 10

Gln Arg Gln Lys Ile Ile Gly Gly
1               5

<210> SEQ ID NO 11
<211> LENGTH: 8
<212> TYPE: PRT
<213> ORGANISM: Homo sapiens

<400> SEQUENCE: 11

Gly Leu Gln Arg Ala Leu Glu Ile
1               5

<210> SEQ ID NO 12
<211> LENGTH: 9
<212> TYPE: PRT
<213> ORGANISM: Homo sapiens

<400> SEQUENCE: 12

Ser Leu Gly Arg Lys Ile Gln Ile Gln
1               5

<210> SEQ ID NO 13
<211> LENGTH: 8
<212> TYPE: PRT
<213> ORGANISM: Homo sapiens

<400> SEQUENCE: 13

Arg Arg Arg Arg Ser Val Gln Leu
1               5

<210> SEQ ID NO 14
<211> LENGTH: 4
<212> TYPE: PRT
<213> ORGANISM: Homo sapiens

<400> SEQUENCE: 14

Ile Ile Gly Gly
1

<210> SEQ ID NO 15
<211> LENGTH: 4
<212> TYPE: PRT
<213> ORGANISM: Homo sapiens
```

```
<400> SEQUENCE: 15

Pro Arg Phe Lys
1

<210> SEQ ID NO 16
<211> LENGTH: 7
<212> TYPE: PRT
<213> ORGANISM: Artificial
<220> FEATURE:
<223> OTHER INFORMATION: activation site

<400> SEQUENCE: 16

Gly Leu Arg Ile Ile Gly Gly
1               5

<210> SEQ ID NO 17
<211> LENGTH: 7
<212> TYPE: PRT
<213> ORGANISM: Artificial
<220> FEATURE:
<223> OTHER INFORMATION: activation site

<400> SEQUENCE: 17

Leu Thr Arg Ile Val Gly Gly
1               5

<210> SEQ ID NO 18
<211> LENGTH: 6
<212> TYPE: PRT
<213> ORGANISM: Artificial
<220> FEATURE:
<223> OTHER INFORMATION: activation site

<400> SEQUENCE: 18

Leu Gly Arg Ile Ile Gly
1               5

<210> SEQ ID NO 19
<211> LENGTH: 6
<212> TYPE: PRT
<213> ORGANISM: Homo sapiens

<400> SEQUENCE: 19

Leu Gly Lys Ile Ile Gly
1               5

<210> SEQ ID NO 20
<211> LENGTH: 7
<212> TYPE: PRT
<213> ORGANISM: Homo sapiens

<400> SEQUENCE: 20

Leu Gln Arg Ile Ile Gly Gly
1               5

<210> SEQ ID NO 21
<211> LENGTH: 7
<212> TYPE: PRT
<213> ORGANISM: Artificial
<220> FEATURE:
<223> OTHER INFORMATION: activation site

<400> SEQUENCE: 21

Leu Gln Lys Ile Ile Gly Gly
1               5
```

```
<210> SEQ ID NO 22
<211> LENGTH: 7
<212> TYPE: PRT
<213> ORGANISM: Artificial
<220> FEATURE:
<223> OTHER INFORMATION: activation site

<400> SEQUENCE: 22

Arg Gln Arg Ile Ile Gly Gly
1               5

<210> SEQ ID NO 23
<211> LENGTH: 7
<212> TYPE: PRT
<213> ORGANISM: Artificial
<220> FEATURE:
<223> OTHER INFORMATION: activation site

<400> SEQUENCE: 23

Arg Gln Lys Ile Ile Gly Gly
1               5

<210> SEQ ID NO 24
<211> LENGTH: 4
<212> TYPE: PRT
<213> ORGANISM: Artificial
<220> FEATURE:
<223> OTHER INFORMATION: collagenase-specific cleavage site

<400> SEQUENCE: 24

Arg Pro Leu Gly
1

<210> SEQ ID NO 25
<211> LENGTH: 21
<212> TYPE: DNA
<213> ORGANISM: Artificial
<220> FEATURE:
<223> OTHER INFORMATION: primer

<400> SEQUENCE: 25
accatcgata accagccctg g                                              21

<210> SEQ ID NO 26
<211> LENGTH: 21
<212> TYPE: DNA
<213> ORGANISM: Artificial
<220> FEATURE:
<223> OTHER INFORMATION: primer

<400> SEQUENCE: 26
ccgcctcgag gtcttttggc c                                              21

<210> SEQ ID NO 27
<211> LENGTH: 7
<212> TYPE: PRT
<213> ORGANISM: Homo sapiens
<220> FEATURE:
<221> NAME/KEY: -
<222> LOCATION: (1)..(7)
<223> OTHER INFORMATION: /note="MASP cleavage site"

<400> SEQUENCE: 27

Arg Phe Lys Ile Ile Gly Gly
1               5
```

```
<210> SEQ ID NO 28
<211> LENGTH: 7
<212> TYPE: PRT
<213> ORGANISM: Homo sapiens
<220> FEATURE:
<221> NAME/KEY: -
<222> LOCATION: (1)..(7)
<223> OTHER INFORMATION: /note="MASP cleavage site"

<400> SEQUENCE: 28

Leu Gly Arg Ile Ile Gly Gly
1               5

<210> SEQ ID NO 29
<211> LENGTH: 7
<212> TYPE: PRT
<213> ORGANISM: Homo sapiens
<220> FEATURE:
<221> NAME/KEY: -
<222> LOCATION: (1)..(7)
<223> OTHER INFORMATION: /note="MASP cleavage site"

<400> SEQUENCE: 29

Leu Gly Lys Ile Ile Gly Gly
1               5

<210> SEQ ID NO 30
<211> LENGTH: 4
<212> TYPE: PRT
<213> ORGANISM: Artificial
<220> FEATURE:
<223> OTHER INFORMATION: caspase substrate

<400> SEQUENCE: 30

Asp Glu Val Asp
1
```

METHOD FOR THE FUNCTIONAL DETERMINATION OF MANNAN-BINDING-LECTIN ASSOCIATED SERINE PROTEASES (MASPS) AND COMPLEXES THEREOF

This application is a §371 national phase filing of PCT/NL2005/000874 filed Dec. 19, 2005, and claims priority to European application No. 04 078 507.3 filed Dec. 23, 2004.

This invention relates to the field of determining, assaying or quantifying activity of components of the complement system. More particularly, the invention relates to methods for detecting the presence or level of activity in a sample of mannan-binding-lectin associated serine proteases (MASPs) or complexes of such proteases with lectins and to detection of lectins themselves. The invention also concerns a recombinant pro-enzyme that can be proteolytically activated as a substrate by MASPs. The activity of the resulting activated pro-enzyme is a measure of MASP activity in a sample. The invention also provides an assay kit containing such a pro-enzyme and expression vectors encoding the modified pro-enzyme.

The complement system is a defense system of the body that can recognize and kill bacteria, yeast, fungi and other micro-organisms and altered host cells. It consists of about twenty plasma proteins that function either as enzymes or as binding proteins. In addition to these plasma proteins, the complement system includes multiple distinct cell-surface receptors that exhibit specificity for the physiological fragments of complement proteins and that occur on a wide range of cell types. There are also several regulatory membrane proteins that function to prevent autologous complement activation and protect host cells from accidental complement attack. The complement system can be divided in three pathways based on different ways of target recognition. In the recently identified lectin pathway, recognition is mediated by lectins such as Mannan-Binding-Lectin (MBL) and ficolins. MBL recognizes uncharged carbohydrates like mannose, fucose and N-acetyl-glucosamine, whereas L-ficolin also known as ficolin/P35 has a high affinity for N-acetyl-glucosamine, but not mannose. The lectins can bind to bacteria, viruses, fungi, protozoa and altered cells by interaction with carbohydrates occurring in repeating patterns on cell surfaces.

MBL and L-ficolin can form complexes with a group of related serine proteases, the mannan-binding-lectin associated serine proteases (MASPs). In the carbohydrate-lectin-MASP complex, the MASP enzyme is activated to yield an active serine protease. The mechanism of MASP activation has not been completely elucidated, but is most likely similar to the activation of the complement component C1r/C1s. Active MASPs can activate other complement components and ultimately lead to activation ot complement component C3 that can ultimately lead to killing of the target (micro-organism, or cell).

Deficiencies in the lectin MBL are relatively frequent and may lead to an increased sensitivity to infection, which is especially problematic in individuals with a non-properly functioning adaptive immune system, such as young children and patients receiving immunosuppressive treatment. The role of the other lectins is less clear. Deficiencies in the proteases (e.g. MASP) also occur. Determination of MBL and/or MASPs can thus be of importance for diagnosis of disorders of the immune system and may provide clues for adaptation in treatment to prevent infections in case of deficiencies.

Methods for detecting MBL, MASPs or MBL-MASP complexes are known. (Roos et al. Eur. J. Immunol. 2004 34: 2589-2598; Roos et al. Mol. Immunol. 2003 39:655-668; Petersen et al. J Immunol Methods. 2001;257:107-16; Thiel et al. Immunobiology. 2002;205:446-454; Moller-Kristensen et al. J Immunol Methods. 2003 ;282:159-167; Stengaard-Pedersen et al. N Engl J Med. 2003;349:554-560) Regular immunoassays such as ELISA can be employed to determine deficiencies that involve lower concentrations of these proteins. However, deficiencies leading to lower intrinsic activity or functionality of the proteins can not be detected by such methods. Therefore, functional assays that measure the biologically relevant activities of MBL and/or MASP and not merely their presence or concentration are preferred.

Functional assays for MBL-MASP complexes and MASP have been described. In many cases, such assays are based on activation of complement component C4 and the assay readout is performed by immuno-assay or haemolytic assays. The assays employing C4 activation are elaborate and require much handling, furthermore they use C4, C4 preparations from (human) blood, or even blood cells leading to hampered reproducibility and possibility of contamination with harmful viruses.

Synthetic peptide substrates for MASP have been developed. Such substrates typically consist of a short peptide sequence that can be recognized and cleaved by MASP. Generally this peptide is coupled to a chromogenic or fluorogenic leaving group. Cleavage of such peptide substrates by MASP results in colour formation or appearance of fluorescence (see for example U.S. Pat. No. 6,235,494 and Presanis et al. (2003) Mol Immunol. 40, pp.921-929). Although the assays employing synthetic peptide substrates do not have the problems associated with the use of C4 as a substrate, they are often not sensitive enough and/or lack sufficient specificity for application in complex biological samples.

Thus, there is a clear (clinical) need for assays that allow for a specific and sensitive detection of (MBL-)MASP activity in a sample.

The present inventors surprisingly found that the serine protease pro-urokinase (also referred to as pro-uPA) is a substrate for active MASP. Cleavage of pro-uroidnase at its activation site results in an active urokinase, whose activity is easily detectable and quantifiable using known synthetic peptide substrates. Thus, the presence of a MASP cleavage site in pro-urokinase allows for the indirect detection of MASP activity by measuring the MASP-mediated proteolytic activation of pro-urokinase as "reporter enzyme" into an active urokinase enzyme.

The invention provides a method for determining the activity of a mannan-binding-lectin associated serine protease (MASP) in a sample, comprising incubating a sample with a pro-urokinase comprising in its activation site the consensus sequence Arg/Leu/Gly-Yyy-Arg/Lys-Ile/Leu/Val-Zzz-Gly-Gly (SEQ ID NO:1) cleavable by a MASP, wherein Yyy can be any amino acid and Zzz is an aliphatic amino acid, and determining proteolytic activation of said pro-urokinase. Preferably, Zzz is Ile, Leu or Val, more preferably Zzz is Ile. The bond split upon activation of naturally occurring pro-urokinase is the peptide bond between Lys (Lys158) and Ile (Ile159) within the cleavage site sequence Pro-Arg-Phe-Lys-Ile-Ile-Gly-Gly (SEQ ID NO:2) (Kasai et al. J Biol Chem 1985; 260:12382-12389).

In a preferred embodiment, a method comprises incubating a sample with a pro-urokinase comprising in its activation site the activation sequence as found in native pro-urokinase. More preferred, naturally occurring (i.e. wild-type) pro-urokinase is used as reporter enzyme in a MASP activity assay as provided herein. However, a mutant pro-urokinase comprising the consensus sequence Arg/Leu/Gly-Yyy-Arg/Lys-Ile/Leu/Val-Zzz-Gly-Gly (SEQ ID NO:1) described above may also be used as reporter enzyme. The sequences of the activation sites of eight different pro-urokinase mutants (herein also referred to as derivatives) that are MASP substrates are known. For example, a method of the invention uses as reported enzyme a pro-urokinase comprising in its activation site a sequence selected from the group consisting of the sequences Arg-Gly-Leu-Arg-Ile-Ile-Gly-Gly (substrate 1) (SEQ ID NO: 3); Asn-Leu-Thr-Arg-Ile-Val-Gly-Gly (substrate 2) (SEQ ID NO:4); Ser-Leu-Gly-Arg-Ile-Ile-Gly-Gly (substrate 3) (SEQ ID NO: 5); Ser-Leu-Gly-Lys-Ile-Ile-Gly-Gly (substrate 4) (SEQ ID NO: 6); Gly-Leu-Gln-Arg-Ile-Ile-Gly-Gly (substrate 5) (SEQ ID NO: 7); Gly-Leu-Gln-Lys-Ile-Ile-Gly-Gly (substrate 6) (SEQ ID NO: 8); Gln-Arg-Gln-Arg-Ile-Ile-Gly-Gly (substrate 7) (SEQ ID NO: 9) and Gln-Arg-Gln-Lys-Ile-Ile-Gly-Gly (substrate 8) (SEQ ID NO: 10). Wild-type or mutant pro-urokinase is easily obtained from mammalian host cells transfected with a nucleic acid construct encoding said pro-urokinase (see Example 1).

The finding that natural wild-type pro-urokinase is a substrate for MASPs is surprising, since the activation sequence of this pro-urokinase form does not resemble the cleavage site sequences in known natural MASP substrates or in known (synthetic) peptide substrates cleavable by MASPs. For example, complement component C4 is cleaved by MASP at the cleavage site sequence Gly-Leu-Gln-Arg-↓-Ala-Leu-Glu-Ile (site of hydrolysis indicated by ↓)(SEQ ID NO:11); complement component C2 at the cleavage site sequence Ser-Leu-Gly-Arg-↓-Lys-Ile-Gln-Ile-Gln (SEQ ID NO: 12) and complement component C3 within the cleavage site sequence Arg-Arg-Arg-Arg-↓-Ser-Val-Gln-Leu (SEQ ID NO: 13), all of which are clearly distinct from the native pro-urokinase activation/cleavage site or a derivative thereof as disclosed herein.

Also encompassed are pro-urokinase mutants with one or more modifications outside of the activation sequence. Modification of native pro-urokinase can, alternatively or additionally, also be in other parts of the enzyme and not near the activation site under the provision that the enzyme retains its enzymatic activity. Such secondary modifications could be directed on improving the properties of the pro-enzyme for the particular application. Useful modifications include modifications increasing the (thermal) stability of the pro-enzyme, conferring resistance to other proteases than MASP, conferring resistance to (naturally) occurring inhibitors, conferring reactivity to certain binding partners (e.g. antibodies or ligands), aiding expression or purification etc.

The present finding that pro-urokinase is advantageously used as MASP substrate in a functional MASP detection assay can be extended further to the design of a MASP cleavable pro-enzyme other than pro-urokinase. Such an enzyme can then also be used as reporter enzyme in a functional MASP assay. To that end, the MASP activation sequence of pro-urokinase can be introduced (either by insertion or replacement) in the non-pro-urokinase pro-enzyme to allow for proteolytic activation of the pro-enzyme by a MASP. Because pro-enzymes are normally activated by proteolysis and their activation sites are usually known, it will be clear at which site to modify a pro-enzyme with a pro-urokinase activation sequence. In one embodiment, a non-urokinase pro-enzyme is modified with the consensus sequence Arg/Leu/Gly-Yyy-Arg/Lys-Ile/Leu/Val-Zzz-Gly-Gly (SEQ ID NO: 1) cleavable by a MASP, wherein Yyy can be any amino acid and wherein Zzz is an aliphatic amino acid. For example, the 8-amino acid activation sequence found in pro-urokinase is used to replace the activation sequence by which the pro-enzyme is normally activated. However, it is also possible to use a stretch of amino acids with less than eight residues because it appeared that the last four amino acid residues (Ile-Ile-Gly-Gly) (SEQ ID NO: 14) of the pro-urokinase activation sequence are not crucial for recognition and cleavage by a MASP. Some residues at the end of the natural pro-urokinase cleavage site may thus be omitted without losing its suitability as a MASP substrate. Accordingly, the invention also relates to a method for determining the activity of a mannan-binding-lectin associated serine protease (MASP) in a sample, comprising incubating a sample with a recombinant non-pro-urokinase pro-enzyme which can be cleaved at the activation site by MASP to release an active enzyme, wherein said activation site comprises the activation sequence Arg/Leu/Gly-Yyy-Arg/Lys, Yyy being any amino acid, and determining proteolytic activation of said pro-enzyme. For example, a suitable activation sequence comprises the sequence Pro-Arg-Phe-Lys (SEQ ID NO: 15) or Arg-Phe-Lys as is found in native pro-urokinase, or a mutated version thereof for example wherein Arg is substituted by Leu or Gly and /or wherein Lys is substituted by Arg. The person skilled in the art will be able to systematically substitute, delete or add one or more amino acid residues and test whether the sequence is cleavable by a MASP. The term 'recombinant' is used herein to refer to a non-naturally occurring protein, i.e. a protein that can only be made by virtue of recombinant DNA technology.

A recombinant non-pro-urokinase pro-enzyme can essentially be any type of enzyme, as long as it is inactive in its pro-form and active in its cleaved form. Of course, pro-enzymes whose activation can be readily detected are preferred. For example, the pro-enzyme is a lipase or a protease wherein the original cleavage site of the lipase or protease is replaced by a cleavage site sequence derived from pro-urokinase. In case the reporter enzyme is a protease, (synthetic) peptide substrates which release a detectable group or label upon hydrolysis by the activated pro-protease are particularly useful in a method of the invention. Examples of such peptide substrates are those with a chromogenic or fluorogenic group. Preferred pro-enzymes are proteases selected from the groups consisting of serine proteases other than pro-urokinase, cysteine proteases, aspartic proteases and metalloproteases. In one embodiment, the pro-enzyme is a pro-caspase. Caspases are synthesized as inactive pro-enzymes with an N-terminal prodomain and two subunits sometimes separated by a linker peptide. During maturation the prodomain and the linker peptide are cleaved at specific Asp residues, resulting in the active caspase of two subunits. Family members are sequentially activated in a proteolytic cascade.

In one aspect, the invention provides a pro-caspase provided with a MASP cleavage sequence derived from pro-urokinase as described above in or near its activation site. This recombinant non-pro-urokinase pro-enzyme is a suitable reporter enzyme to detect MASP activity using a coloured or fluorescent caspase substrate, many of which are commercially available (see for example www.biomol.com).

The recombinant pro-caspase can be derived from a pro-caspase by replacing its activation site by an activation site which is cleavable by MASP as described above, such as by removing its 'natural' activation site and inserting, not necessarily on the same position, a pro-urokinase activation site. The recombinant pro-caspase is preferably selected from the group consisting of pro-caspase-1, pro-caspase-3, pro-caspase-7, pro-caspase-8, pro-caspase-9, and pro-caspase-10. Preferably, the MASP cleavage sequence is introduced within a distance of up to 30 amino acid residues, preferably up to 20 residues, more preferably up to 10 residues, from the natural activation site of said pro-caspase. This ensures that cleavage by MASP releases an active caspase.

One embodiment of the invention which is particularly useful is a method wherein said recombinant non-urokinase pro-caspase is pro-caspase-3 or pro-caspase-7. Preferably, residue D175 in pro-caspase-3 or residue D198 in wild-type pro-caspase-7 is replaced by the activation sequence Arg/Leu/Gly-Yyy-Arg/Lys, Yyy being any amino acid. The invention also provides the modified pro-caspase per se, more particularly a modified pro-caspase derived from a pro-caspase by replacing its natural activation site or replacing an amino acid sequence in the region of its natural activation site by the activation sequence Arg/Leu/Gly-Yyy-Arg/Lys cleavable by MASP, or alternatively to insert such a MASP cleavage sequence in the natural sequence of the pro-caspase.

As will be clear from the above, MASP-mediated cleavage of the reporter enzyme, (either wild-type pro-urokinase, a mutant pro-urokinase or a recombinant non-urokinase pro-enzyme) results in the proteolytic activation of the reporter enzyme. The extent of pro-enzyme activation is a measure for the amount of active MASP.

Activation of pro-urokinase or a functional derivative thereof can be detected by virtue of known urokinase peptide substrates (see e.g. EP 691 409). Such peptide substrates typically consist of a short amino acid sequence, often 3 amino acid residues, coupled to a chromogenic, fluorogenic or luminogenic leaving group. Enzymatic action of active urokinase (derivative) results in formation of a coloured, fluorescent, or light emitting compound, that can be detected with readily available equipment. In one embodiment, said peptide substrate is a compound Xxx-Yyy-Arg-pNA, wherein Xxx and Yyy can be any amino acid and pNA represents a para-nitroaniline moiety. For example, the chromogenic substrate pyro-Glu-Gly-Arg-pNA (S-2444 from Chromogenix, Milan, Italy) is suitably used in a method of the invention to evaluate MASP-induced activation of a pro-urokinase.

In another embodiment, urokinase activity is evaluated using plasminogen as a substrate. Plasminogen, a single chain glycoprotein zymogen, is the precursor the fibrinolytic enzyme plasmin. The native form of plasminogen is composed of 791 amino acids with glutamic acid located at the N-terminal portion (Glu-plasminogen). Plasminogen cleavage by urokinase (or a derivative thereof) can be detected in a method provided herein using a plasmin-specific peptide substrate which releases a detectable label upon hydrolysis by plasmin, for example D-valyl-L-leucyl-L-lysine 4-nitroanilide.

MASP-mediated activation of pro-caspases can be easily detected using reagents known in the art. The caspase substrate is typically a synthetic compound which comprises an amino acid sequence which is cleavable by caspase and which further has a part that can be easily detected after cleavage. Examples of such substrates and sequences of some known caspase substrates are given in EP 1443116. Preferably used is a compound comprising the amino acid sequence Asp-Glu-Val-Asp-pNA (SEQ ID NO:30), in which pNA is p-nitroanilide.

A person skilled in the art will recognize that the invention can be used in a variety of assay formats. These do not only include measurements or detection of activity of MASPS, or lectin-MASP complexes but also, as will be described below, detection of a lectin itself using exogenous MASP.

If MASPs are present in a sample in a relatively purified or concentrated form, simple mixing of MASP, a pro-enzyme (e.g. a pro-urokinase or recombinant non-urokinase pro-enzyme) and peptide-substrate in a suitable buffer-system might be sufficient.

A sample can be a biological fluid, a fraction of a biological fluid, a biological tissue or an extract thereof, or a fraction of an extract of a biological tissue. Typically, MASP activity is conveniently assayed using a serum sample. Citrate or EDTA plasma could also be used if extra calcium is added. In biological samples MASPs can be present in a free form, or in a complex with other proteins such as lectins, like MBL and ficolins. Also, the sample may contain inhibiting or interfering compounds. Therefore, MASP activity is preferably not detected in the crude (biological) sample but in another type of format that is not prone to interference with the assay performance. In one embodiment, the activity is measured in a format wherein MASP or a complex comprising MASP is captured from a sample using a specific binding molecule. Preferably, said binding molecule is specific for a particular MASP and does not interfere with MASP activity. Use of a binding molecule can increase the specificity of the assay. It is often advantageous to use a binding molecule that is or can be immobilized on a solid surface, for example on the bottom of a well of a microtiter plate. One of the possibilities is an immunocapture format, wherein a surface (plate, membrane) is provided with a binding molecule, such as an antibody, and the (biological) sample is brought in contact with the surface-bound antibody for some time, typically 1-24 h, followed by washing with a suitable buffer with additions like detergents and/or proteins. Bovine serum albumin (BSA), gelatin or casein can be used. After a washing step to remove non-specifically bound molecules, a pro-enzyme can be added together with a suitable peptide substrate in a suitable buffer and hydrolysis of the substrate is monitored, e.g. by colour formation. The resulting colour is a measure for the activity of MASP in the sample. Depending on the specificity of the antibody used for capture, either free MASP and/or MASP in complex with lectins like MBL and/or ficolins can be detected. The use of an antibody also allows to discriminate between the activity of various MASP forms, like MASP-1, MASP-2 and MASP-3, depending on the specificity of the antibody used. It is also possible to use combinations of two or more different binding molecules to capture MASPs. Antibodies for MASP have been described, see for example Moller-Kristensen et al. J Immunol Methods 2003;282:159-167. Some of these antibodies are commercially available. In another embodiment of the invention, a binding molecule capable of specifically binding to a lectin is used, for example an antibody to MBL or ficolins. After contact with a biological sample, the particular lectin, but also complexes of that lectin with MASPs can be captured and immobilized. After this capture step, determination of reporter enzyme conversion as described above can follow. The final result is a signal whose intensity or strength is proportional to the amount of active MASP that is present in the complex with the particular lectin.

Instead of an antibody for capturing a lectin, also an immobilized carbohydrate can be used as specific binding molecule. A plate coated with mannan (a polymeric carbohydrate from yeast) can be employed for a functional determination of MBL-MASP-complexes. In a similar way complexes with other lectins can be captured by using a suitable immobilized carbohydrate.

Such determinations can also be adapted to detect a lectin in a sample, e.g. by addition of an excess of (purified) MASP to the immobilized lectin such that lectin/MASP complexes are formed. Provided that MASP only becomes immobilized when it is complexed to an immobilized lectin, and that the capture/immobilization step is specific for a certain lectin, captured MASP activity is a measure for the amount of lectin present in the sample. It will be clear that all these embodiments of the invention have in common that a pro-enzyme comprising a pro-urokinase activation sequence (or a variant thereof is used as a substrate to detect MASP activity.

A person skilled in the art will understand that the specific embodiments described above are certainly not the only possibilities and that other, similar methods can also be used to detect molecules inhibiting MASP activity, or inhibiting the interaction of a particular lectin with either MASP or with carbohydrate. Each application may have its own optimal conditions such as pH, ionic strength, buffer composition etc., which can be easily determined experimentally by one skilled in the art.

The invention also provides a recombinant pro-urokinase comprising in its activation site the consensus sequence Arg/Leu/Gly-Yyy-Arg/Lys-Ile/Leu/Val-Zzz-Gly-Gly (SEQ ID NO: 1) cleavable by a MASP, wherein Yyy can be any amino acid and Zzz is an aliphatic amino acid and wherein said activation sequence is different from the natural activation site of pro-urokinase.

A recombinant pro-urokinase is advantageously used as reporter enzyme in a MASP activity assay as disclosed herein. In a preferred embodiment, a recombinant pro-urokinase comprises a recognition sequence selected from the group consisting of Gly-Leu-Arg-Ile-Ile-Gly-Gly (SEQ ID NO: 16); Leu-Thr-Arg-Ile-Val-Gly-Gly (SEQ ID NO: 17); Leu-Gly-Arg-Ile-Ile-Gly (SEQ ID NO: 18); Leu-Gly-Lys-Ile-Ile-Gly (SEQ ID NO: 19); Leu-Gln-Arg-Ile-Ile-Gly-Gly (SEQ ID NO: 20); Leu-Gln-Lys-Ile-Ile-Gly-Gly (SEQ ID NO: 21); Arg-Gln-Arg-Ile-Ile-Gly-Gly (SEQ ID NO: 22) and Arg-Gln-Lys-Ile-Ile-Gly-Gly (SEQ ID NO: 23).

A recombinant pro-urokinase according to the invention can be obtained using recombinant DNA technology methods known in the art. The cDNA sequence of pro-urokinase is known and can be obtained from publicly available databases. Such a cDNA can be obtained with existing technology such as from mRNA isolated from a suitable cell line or tissue by reverse transcriptase polymerase chain reaction (RT-PCR) using primers designed on the basis of the known sequence. Many alternative procedures are known in the art to obtain a specific cDNA sequence. The coding sequence can be adapted to improve later expression into protein and to facilitate later introduction of changes aimed at altering the activation specificity of the resulting pro-enzyme after expression. Also a suitable promoter and other regulatory sequences have to be added as is known in the art. The coding sequence or altered coding sequence is introduced into a vector such as a plasmid or virus to enable introduction into a cell system for expression. Expression can in general be performed in eukaryotic animal cell or yeast expression systems or in prokaryotic bacterial expression systems. These systems are known in the art and are in many cases available in commercial form. After the expression step, procedures to isolate the expressed protein from the cells or, it the pro-enzyme is secreted, from the culture medium are generally required. Very likely further purification of the expressed protein will be required. Many procedures for these steps are known in the art.

When an expression plasmid is constructed containing the natural unmodified coding sequence of pro-urokinase, appropriate modifications can be added by any of the known methods of site directed mutagenesis, or newer methods involving polymerase chain reaction. To ease construction of a large number of different coding sequences differing in the sequences coding for the novel activation site in the expressed protein it might be convenient to introduce some extra alterations in the coding sequence leading to new restriction sites that can be used to introduce many different modifications in the activation site in an easy and quick way by introduction of synthetic oligonucleotides between these restriction sites. These extra alterations can either be so called silent mutations, not altering the amino acid sequence, or changes which alter the protein sequence but have no adverse effects on the protein function. A further advantage of this approach employing newly introduced restriction sites and subsequent oligo insertion, is the lower chance on secondary unwanted mutations that might arise during polymerase chain reaction based methods. In the same way further modifications to improve the properties of the pro-enzyme could be introduced. Thus, the invention also provides for a nucleic acid sequence encoding a recombinant (i.e. modified) pro-urokinase according to the invention.

Another aspect involves the use of pro-urokinase or a non-pro-urokinase pro-enzyme comprising in its activation site the sequence Arg/Leu/Gly-Yyy-Arg/Lys, Yyy being any amino acid, as reporter enzyme for the detection of MASP activity, for example in a clinical sample. The invention is particularly useful for detection of activity of MASP-2 which displays, in contrast to MASP-1, hardly any activity towards traditional low molecular weight peptide substrates (Presanis et al. Mol. Immunol. 2003;40:921-929). The use of a reporter enzyme with a pro-urokinase activation site now allows for a sensitive detection assay for MASP-2 activity, resulting in e.g. shorter assay duration and/or smaller sample volume requirement.

A method of the invention is advantageously used in a clinical setting, for example for the diagnosis or evaluating treatment efficacy in immunocompromised individuals. Furthermore, it can be used in a screening protocol for the identification of compounds capable of modulating MASP, lectins and/or lectin/MASP complexes. For example, inhibitors of the MASP complex can be identified with a method of the invention using naturally occurring pro-urokinase as a reporter enzyme for MASP activity. Other pro-enzymes with a cleavage/activation site that is cleavable by MASP can of course also be used when applying a method of the invention, be it in a clinical or a research setting.

In yet another aspect, the invention provides a kit for use in a method to determine or quantify a particular MASP, MASP-form or lectin containing a recombinant pro-urokinase according to the invention and all necessary materials to perform one or a number of determinations as disclosed in the present invention. Typically, such a kit comprises containers with sufficient quantities of modified pro-enzyme as a reporter enzyme, such as native pro-urokinase or a mutant thereof, a suitable substrate to detect reporter enzyme activity, a suitable standard preparation to quantify MASP activity and materials to prepare buffer solutions. A kit might also contain one or more assay plates in e.g. the regular 96-well, 384-well or 1536-well microtiter plate format. Furthermore, a kit may also contain one or more specific (monoclonal or polyclonal) antibodies or fragments thereof that are reactive with the MASP, lectin or lectin/MASP complex to be detected, or one or more carbohydrate preparations specifically interacting with particular lectins. These antibodies or carbohydrates may be present in the kit in an immobilized form e.g. coated to the wells of a microtiter plate in the conventional 96-well, 384-well or 1536-well format. It might be advantageous to add stabilizers to the modified pro-enzyme to increase its stability during transport and storage. Such stabilizers could be other proteins like albumin or gelatin, carbohydrates like trehalose or mannitol, anti oxidants, detergents or other organic chemicals. Furthermore inorganic salts might also have beneficial effects on stability. Most conveniently the modified pro-enzyme is present in a lyophilized form which has to be reconstituted by adding buffer or water shortly before use. Alternatively a kit or device might be of the "dipstick" type where all necessary reagents present in a dry form are immobilized on a strip or dot of membranous material. In addition, a description how to perform the determination, preparing the samples and calculate the activity may be included.

LEGENDS

FIG. 1. Pro-urokinase is a substrate for MBL-MASP complexes

Purified pro-urokinase derivatives and wild-type pro-urokinase were tested for their suitability as substrates for MBL-MASP complexes. MBL-containing serum (A/A genotype) was diluted in buffer and incubated in a microtiterplate coated with mannan. After a washing step, pro-urokinase (wild-type or a derivative number 1-8) and the urokinase substrate pyro-Glu-Gly-Arg-pNA were added to the wells. Wells without serum were used as control. Colour formation was measured after 2h incubation at 37° C. Surprisingly, the best signal to noise ratio was observed for wild-type pro-urokinase.

FIG. 2.

A mannan-coated microtiter plate was used to bind and immobilize MBL-MASP complexes from heterozygous MBL-deficient serum (A/B genotype), homozygous MBL-deficient serum (B/B genotype) and normal serum (A/A genotype) in various dilutions. After washing, wild-type pro-urokinase or substrate 2 and chromogenic peptide pyro-Glu-Gly-Arg-pNA were added. The absorbance change at 405 nm was followed in time. The slopes of A405 versus time-squared graphs were taken as a measure of activity. Both substrates could be used to detect MASP-activity in normal serum, whereas hardly any or no activity was observed in either A/A or B/B serum.

FIG. 3.

Figure 2:
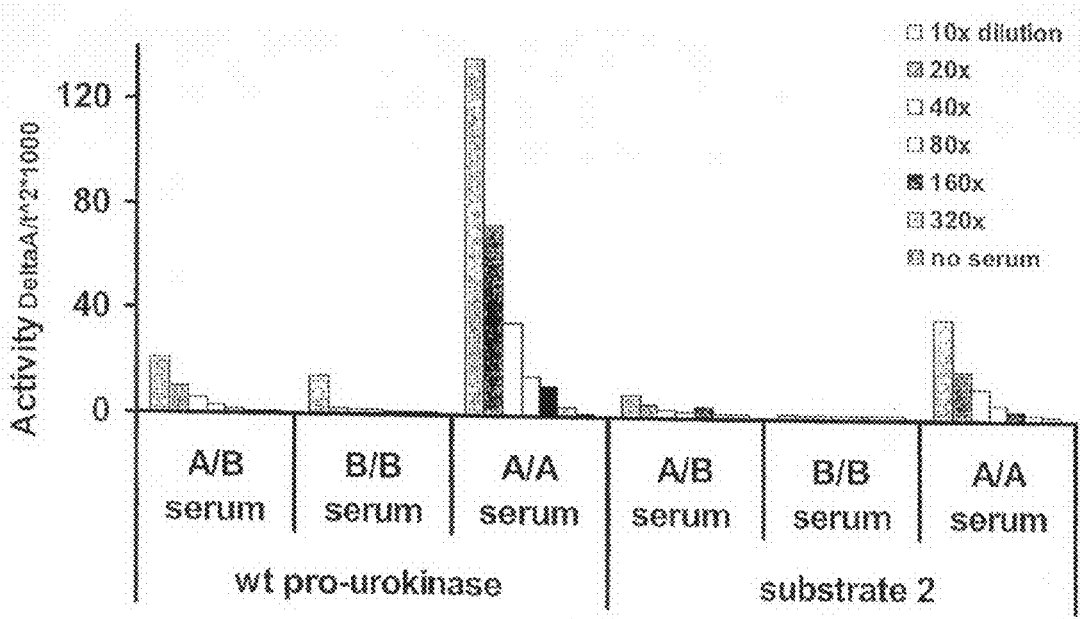

A mannan coated microtiterplate was used to bind MBL-MASP complexes from normal serum A/A genotype (closed triangles-solid line) and homozygous MBL-deficient serum B/B genotype (open triangles dotted line). The activity of MBL-MASP complexes was determined using wild-type pro-urokinase as described in Example 3 and FIG. 2. The binding step was performed in the presence of physiological 0.15 M NaCl (panel A) and in the presence (panel 3) of 1 M NaCl.

FIG. 4.

In this experiment an IgM-coated microtiterplate was used in the binding step instead of a mannan coated plate. Apart from that, the experiment was performed as described in FIG. 3, again in absence (panel A) and presence (panel B) of 1 M NaCl. Normal (A/A genotype) serum (closed triangles; solid line) and homozygous (B/B genotype) MBL-deficient serum (open triangles; dotted line).

FIG. 5.

Figure 3A:
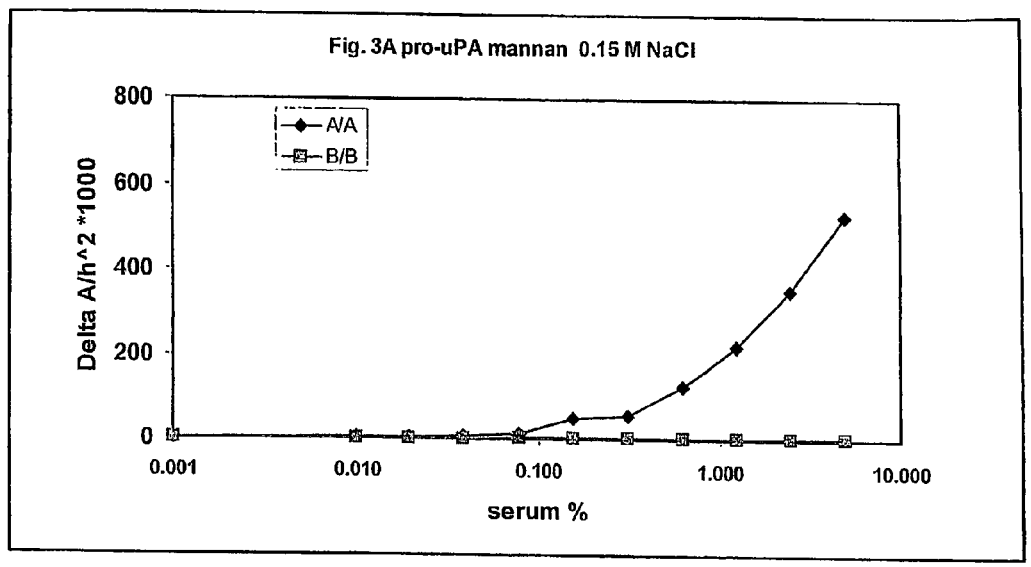
Figure 3B:
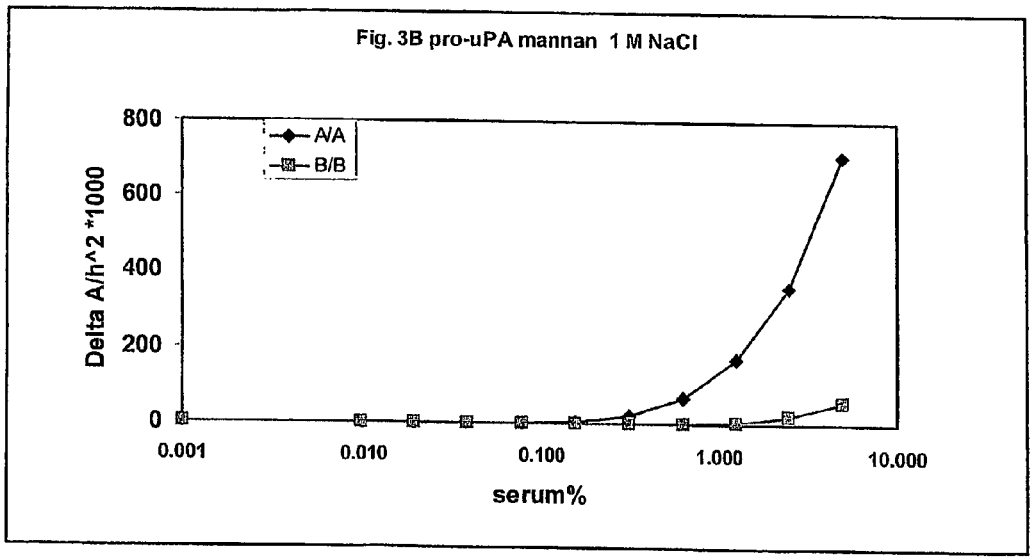

The experiment of FIG. 3 with a mannan coated plate, was repeated with traditional detection via C4 activation and ELISA: using normal (A/A) serum (solid triangles-solid line) and MBL-deficient (B/B) serum (open triangles-dotted line) both in absence (panel A) and presence (panel B) of 1 M NaCl.

FIG. 6.

Figure 4A:
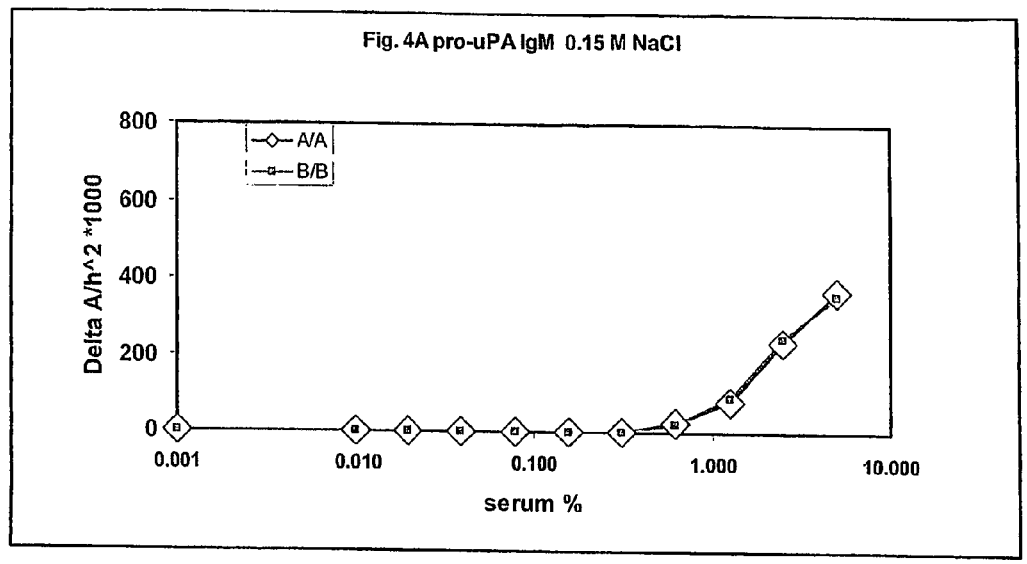
Figure 4B:
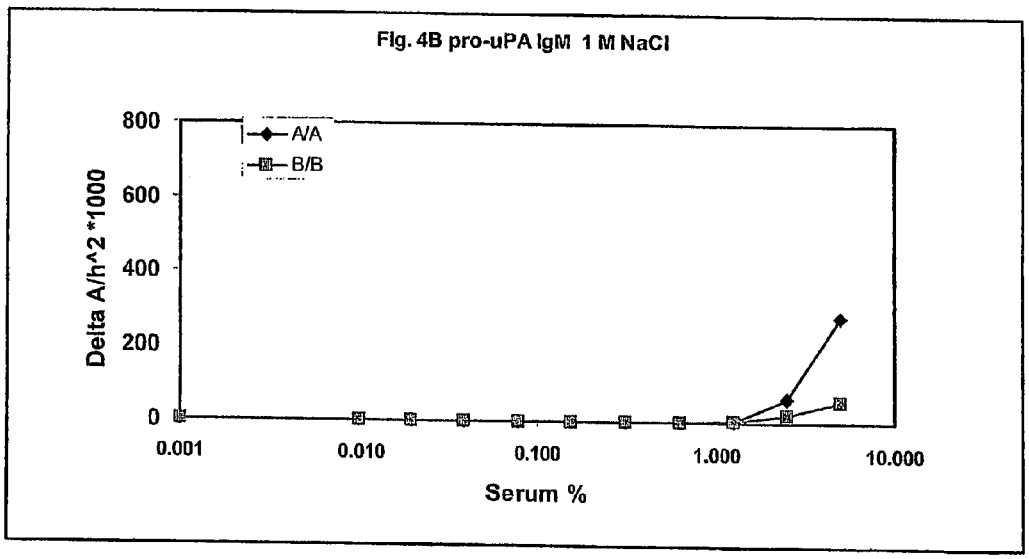

The experiment of FIG. 4 with an IgM-coated plate was repeated with traditional detection via C4 activation and ELISA using normal (A/A) serum (solid triangles-solid line) and MBL deficient (B/B) serum (open triangles-dotted line) both in presence of 0.15 M NaCl (panel A) or presence of 1 M NaCl (panel B).

FIG. 7.

Various dilutions of purified recombinant MASP-2 were tested for their response with wild-type pro-urokinase based detection and substrate 2 (table 1) based detection. MASP-2 was diluted in buffer to which wt pro-urokinase or pro-urokinase derivative 2 was added followed by pyro-Glu-Gly-Arg-pNA. The plate was incubated for 2h and $A^{405}$ was measured (see example 5 for details).

FIG. 8.

The effect of coating with various mannan concentrations on two different types of microtiter plates on response of the assay was investigated. Microtiter plates were coated with 0-1000 µg/ml mannan and used for detection of MBL-MASP complex in normal serum (see example 6).

FIG. 9.

MBL-MASP complexes were captured on a mannan coated plate as described in example 4. After capture, buffer, pro-urokinase and peptide substrate and boroMpg (0-1 µM final concentration) in DMSO, or an equivalent amount of pure DMSO (control) were added and activity was measured. All details were as described in example 4. Activity was expressed as $\Delta A^{405}/h^2 \times 1000$.

FIG. 10.

MBL-MASP complexes from wild-type (A/A) serum and deficient (B/B) serum diluted 50 or 100 fold in buffers of various compositions were captured on a mannan coated plate. Except for the buffer composition, the procedure of Example 4 was followed. After capture, the plate was washed 4 times with 50 mM TrisHCl, 1.5 mM NaCl, 0.5 mM $CaCl_2$, 0.01% (v/v) BRIJ 35™, pH 8.0. After washing, 50 mM TrisHCl, 1.5 mM NaCl, 0.5 mM $CaCl_2$, 0.01% (v/v) BRIJ 35™, pH 8.0, pro-urokinase and peptide substrate were added and activity was measured. All other details were as described in example 8. Activity was expressed as $\Delta A^{405}/h^2 \times 1000$. Buffer components varied are indicated along the x-axis.

FIG. 11.

To mannan coated wells of a microtiterplate 100-fold diluted (A/B) serum in 50 mM Tris.HCl, 75 mM NaCl, 0.5 mM $CaCl_2$, 0.01% (v/v) Brij35™, pH 8.0) was added and incubated during 1 h at 4° C. After washing, purified recombinant MASP-1, MASP-2 and C1r/s in 50 mM Tris,75 mM NaCl, 0.5 mM CaCl2,0.01% Brij35, pH 8.0 or only buffer as control were added and again incubated for 1 h at 4° C. The supernatant was transferred to a new non-coated plate. The capture plate was washed and to both the capture plate and supernatant plate buffer with or without detection enzyme pro-urokinase and pyro-Glu-Gly-Arg-pNA were added. The activities bound to the capture plate and in the supernatant were determined. The activity bound to the capture plate was expressed as percentage of total (bound to plate plus in supernatant). Light bars represent activities measured in a regular way with pro-urokinase and pyro-Glu-Gly-Arg-pNA both present, the dark bars show the activity without pro-urokinase directly on the peptide substrate.

FIG. 12.

Twenty-one serum samples from individuals with known MBL genotype were analysed for MBL-MASP activity using the pro-urokinase method as described in Example 9. Activity was expressed as Delta $A^{405}/h^2 \times 1000$. The difference in the three genotypes, homozygous deficient (B/B), heterozygous deficient (A/B) and normals (A/A) can clearly be seen.

FIG. 13.

The level of MBL-MASP complex activity was measured with the new pro-urokinase activation method and the traditional C4 activation method. Details can be found in Example 10. The results show a strong correlation between both methods.

EXAMPLES

The following examples are merely intended to illustrate the invention.

Example 1

Preparation of Pro-urokinase Derivatives

Preparation of pro-urokinase-derived reporter enzymes for determination of MASP activity.

Construction of Expression Plasmid for Pro-urokinase Derivatives.

The complete cDNA coding for human pro-urokinase (UKcol) with a collagenase-specific cleavage site Arg Pro Leu Gly (SEQ ID NO: 24) (RPLG in one-letter code) was excised from expression plasmid pEV2UKcol (see EP 0691409 B1 for details) and cloned into the multiple cloning site of a new expression vector containing a neomycin resistance marker pcDNA3 (Invitrogen).

With polymerase chain reaction using primers 5'- ACC ATC AAC Gat AAC CAG CCC TGG-3' (SEQ ID NO:25) and 5'-CCG CCT cga gGT CTT TTG GCC-3' (SEQ ID NO:26) (mutations indicated as lower case letters) two new unique restrictions sites ClaI and XhoI were introduced flanking the region coding for the activation site. The introduction of these restriction sites leads to a replacement of Leucine-153 to Serine in the resulting pro-urokinase derivative. This mutation was found to have no detectable effect on the properties of the pro-urokinase. The resulting plasmid vector was used to construct vectors coding for pro-urokinase based detection enzymes by digesting the plasmid with ClaI and XhoI, followed by insertion and ligation of two partially complementary oligonucleotides coding for the required mutated amino acid sequence. For construction of a detection enzyme with potential MASP recognition and cleavage sites two partially complementary oligonucleotides were inserted in the ClaI/XhoI digested plasmid.

The resulting plasmids, coding for various pro-urokinase detection enzymes with new recognition cleavage sequences, were used to transfect Chinese hamster ovary (CHO) cells to express the various pro-urokinase derivatives.

Expression of Pro-urokinase Derivatives.

Cells (Chinese Hamster Ovary, CHO or Human Embryonic Kidney, HEK) were grown to 70-90% confluence in culture dishes. 1 µg of the various plasmids coding for pro-urokinase derivatives was mixed with medium and Fugene 6™ (Roche) and transfection was performed according to the manufacturer's instructions. Stable transfectants were selected by resistance to the neomycin analog G418. Transfected cells were cultured at various dilutions in medium containing the selection agent G418 (1 mg/ml) for 1-2 weeks. Surviving clones were selected, isolated with a pipette and cultured separately in medium containing the selection agent. Expression of pro-urokinase variants by these clones was tested by immunoassay (van Bohemen et al. Fibrinolysis 9 (1995) 343-349). Clones with high expression levels were expanded and used for production, in culture disks, flasks, cell factories, or any other suitable system known to one skilled in the art. For production, cells were routinely grown in triple flasks and conditioned culture medium was collected, centrifuged and stored at −20° C. The pro-urokinase based detection enzymes were purified according to the methods described previously (J H Verheijen et al. Biochem J 323 (1997) 603-609).

The sequences inserted in the activation region of pro-urokinase included parts of natural MASP cleavage sequences such as those occurring in the natural MASP substrates, complement factors C4 and C2 and sequences of peptides known to be substrates for MASPs (based on U.S. Pat. No. 6,235,494) and additionally a C1r sequence. All these sequences contain an arginine (R) residue at the cleavage site. From some sequences we also constructed the non-natural equivalents with lysine (K) residues instead of arginine residues at the cleavage position. Apart from these sequences, based on existing natural and synthetic MASP substrates, also a few non-MASP-specific sequences were added as negative controls. The natural activation cleavage site of wild-type pro-urokinase was added as a control (Table 1; wt).

Example 2

Efficacy of Pro-urokinase Derivatives for Detection of MASP Activity.

The purified pro-urokinase derivatives with cleavage sequences were tested for efficacy as substrates for MASPs as described below.

A microtiterplate (Nunc Maxisorb) was coated with 100 microliter per well mannan at 50 µg/ml in 0.1 M Na-carbonate buffer pH 9.6 at 37° C. for 2 h. Subsequently the plate was washed four times with Na-phosphate pH 7.5, 0.15 M NaCl, 0.05% (v/v) Tween 20™ (PBS/T) and blocked with 10 mM Na-Phosphate pH 7.5, 0.15 M NaCl (PBS), with 1% (w/v) bovine serum albumin and washed with PBS/T.

Human serum, containing MBL and MASPs, was diluted 40 fold in 10 mM barbital, 1.0 M NaCl, 0.1% (w/v) gelatine, 2 mM $CaCl_2$, 2 mM MgCl2 pH 7.3, 0.05% (v/v) Tween20™ (GVB++buffer). Sample wells in the microtiter plate were filled with this diluted serum, control wells were filled with only GVB++buffer. After 1 h incubation at 4° C., to enable binding of MBL-MASP complexes, present in the serum, to the coated microtiter plate and washing the plate with PBS/T+5 mM $CaCl_2$, 100 µl of 50 mM Tris HCl pH 7.6, 1.5 mM NaCl, 0.5 mM $CaCl_2$, 1 µM $ZnCl_2$, 0.01% (v/v) BRIJ35™ was added followed by 10 µl of pro-urokinase derivative at approximately 20 µg/ml and 10 µl of the urokinase peptide substrate pyro-Glu-Gly-Arg-pNA (Chromogenix S2444,) at 6 mM was added. The plate was shaken on a plate shaker and incubated for 2 h at 37° C., after which the absorbance at 405 nm was measured with a microtiter plate reader. The absorbance values at 2 h incubation for serum wells and control wells are shown in FIG. 1. Suitable substrates for MBL-MASP complexes should have a high signal with serum and a low signal without serum. Surprisingly, the best signal to background ratio was found for natural pro-urokinase with the sequence Pro Arg Phe Lys (PRFK) in the activation site. The substrates with sequences similar to the natural substrate sequences of MASPs performed less well. However, for other pro-enzymes as reporter enzyme this may not be the case.

Example 3

Determination of MBL-MASP Complexes in Serum

Based on the results of example 2 an assay for MBL-MASP complexes in serum was developed. Three different sera were used, serum (A/A) with a heterozygous MBL deficiency, serum (B/B) with an homozygous MBL deficiency and a normal serum (A/A). A microtiter plate was coated with mannan, washed and blocked as described in example 2.

Serum samples were diluted 10-320 fold in GVB++buffer (see example 2) and 100 µl of these dilutions were pipetted into wells of the coated microtiter plate. Control wells containing only buffer and no serum were included. The plate was incubated overnight at 4 °C. to enable binding of MBL-MASP complexes from the serum to the plate and subsequently washed 4 times with PBS/T +5 mM $CaCl_2$.

To all wells 100 µl of detection buffer, 10 µl of either wild-type pro-urokinase or pro-urokinase derivative 2 at 7.6 µg/ml and 10 µl of pyro-Glu-Gly-Arg-pNA at 6 mM were added (see example 2). The plate was shaken and $A^{405}$ was followed in time with a microtiter plate reader. The slopes of the graphs of $A^{405}$ versus time squared were calculated and used as a measure of activity.

The results (FIG. 2) show a dose dependent activity in normal (A/A) serum with both substrates, wild-type pro-urokinase and substrate 2. Hardly any activity was found in the homozygous deficient plasma (B/B), whereas only a slight activity could be detected in the heterozygous serum (A/B). The signal with wild-type pro-urokinase was consistently higher than that with substrate 2.

Example 4

Comparison of Novel and Conventional Method to Determine MBL-MASP Activity Levels.

In this example the MBL-MASP levels in various sera were determined, using either a method according to the invention employing natural pro-urokinase as a reporter pro-enzyme or using an existing method employing a C4 preparation from human blood and detection based on the activation of C4 and binding of C4b to the mannan coated plate, followed by an immunological detection of bound C4b (ELISA).

Both the C4 method and the method according to the invention use a microtiterplate coated with mannan (see example 1) to start with. To each well 100 µl of diluted serum was added and incubated and washed as described before. An MBL-positive control serum and an MBL-deficient serum were used.

For existing MASP assays (see for example US 2003/0186419) it has been reported that the presence of 1 M salt is important to ensure that only MASP activity is assayed and not the activity of other proteases, including C1, which are sensitive to high salt concentrations. To test whether the novel functional MASP assay of the invention is also dependent on a high salt concentration, we performed experiments using either GVB++buffer containing 1 M NaCl for dilution, or with the same buffer with 0.15 M NaCl. The results shown in FIGS. 3 to 6 show no effect of high salt, indicating that a method of the invention does not detect C1 activity at a physiological salt concentration.

Pro-urokinase with the natural activation site and the urokinase substrate pyro-Glu-Gly-Arg-pNA were used for detection. Incubation was performed at 37° C. and absorbance change at 405 nm was followed during 2 h. Activity was expressed as absorbance change per h squared and plot against the equivalent amount of serum per well. The results are summarised in FIG. 3 A/B.

Figure 5A:
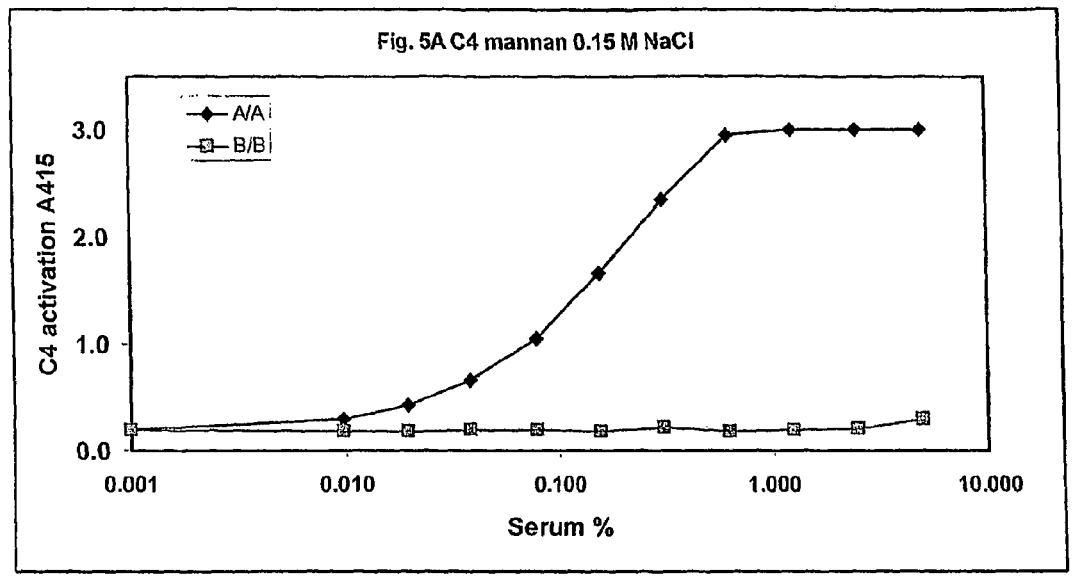
Figure 5B:
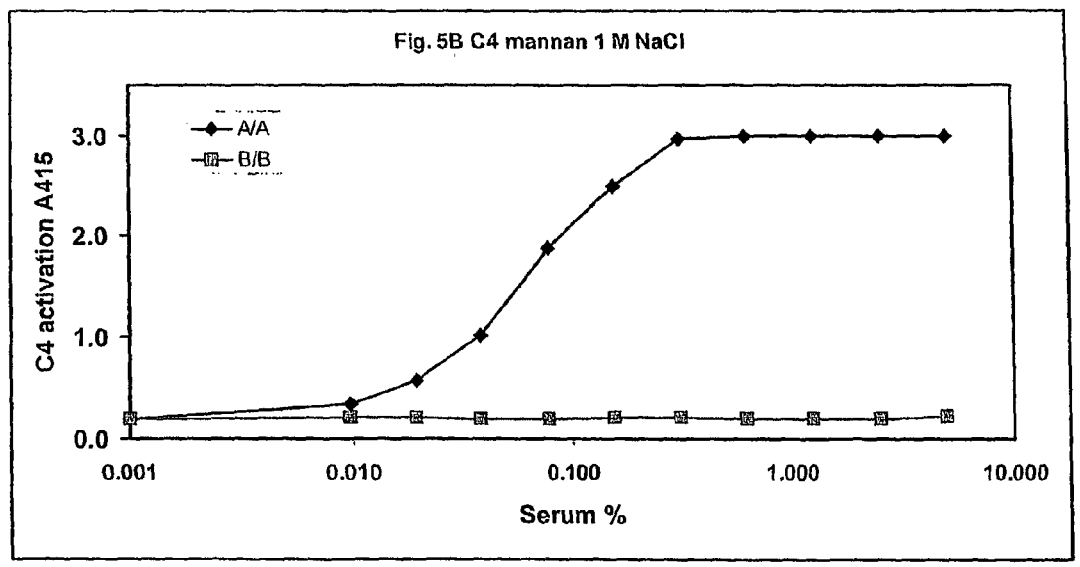

The C4 method was performed as follows. Plates were coated and washed as described above. Hundred microliter of serum dilutions in GVB++ with 1 M NaCl were added and the plate was incubated 1 h at 4° C. The plate was washed with PBS/T+5 mM $CaCl_2$ and a C4 dilution ( 3 microgram/ml) in GVB++ was added. The plate was incubated at 37° C. for 1 h and washed. A digoxigenin labelled C4 specific monoclonal antibody (1/4000), (see Roos et al. Mol Immunol 2003; 39:655-668) in PBS, 1% (w/v) BSA, 0.05% (v/v) Tween™ 20 was added and incubated for 1 h at 37° C., after washing, an horse radish peroxidase labelled Fab fragment specific for digoxigenin (obtained from Roche Applied Science) was added and incubated for 1 h at 37° C., after washing a solution of the peroxide substrate ABTS and 0.03% (v/v) $H_2O_2$ was added. Colour formation at 415 nm was followed for 1 h at room temperature. The results are shown in FIG. 5 A/B.

Figure 6A:
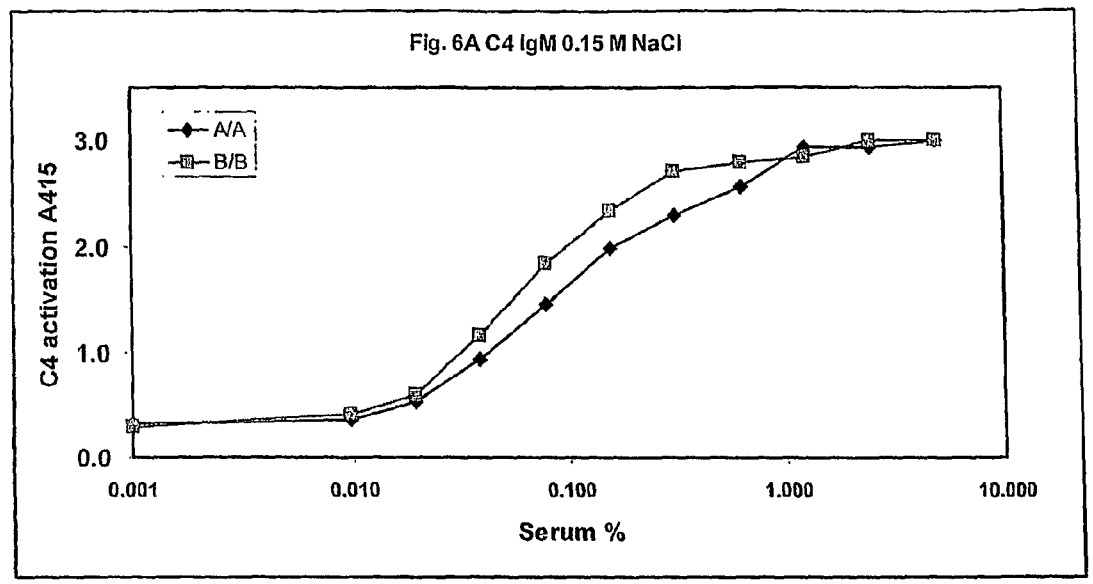
Figure 6B:
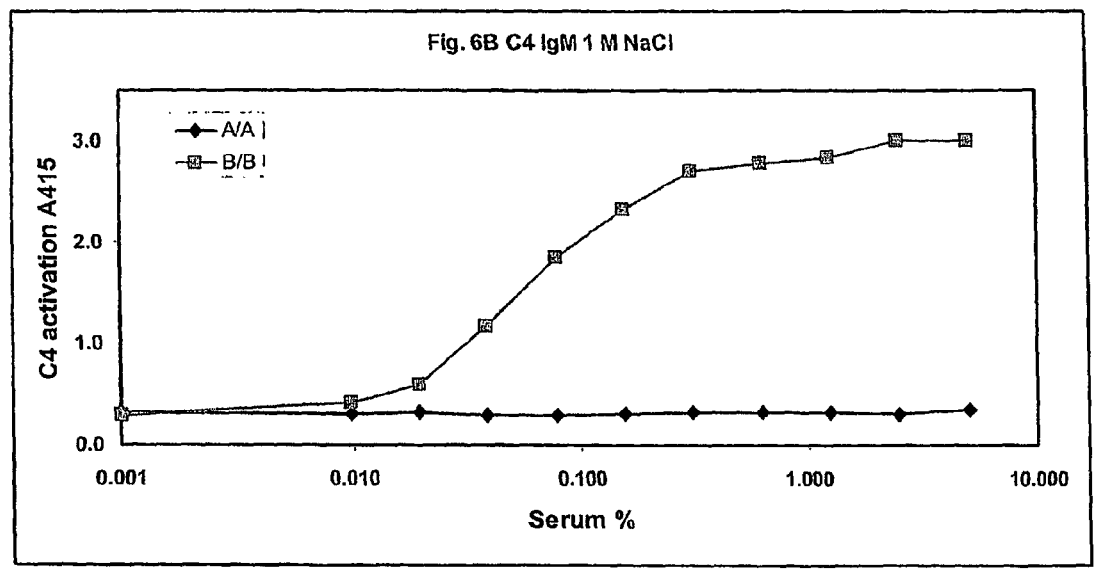

The MASP enzyme shows some homology with the two C1 q-associated serine proteases C1 r and C1 s. It has been shown for some conventional MASP assays that the activity of C1 r and C1 s can disturb the assay. This can be prevented using IgM whose Fc portion binds to the C1 protein and thereby inhibit C1 r and C1 s activation. To investigate whether C1 can act as a disturbing factor in a novel MASP assay according to the invention, which would indicate that the novel assay also detects C1 activity, experiments were performed with plates coated with IgM at 2 µg/ml in carbonate buffer instead of mannan. In FIG. 4 A/B the results are shown for the determination using pro-urokinase in the detection step, whereas in FIG. 6 A/B the results using the C4 method are shown. Both the pro-urokinase method and the C4 method show activity with MBL-containing (homozygous) A/A serum on mannan coated plates. In both cases the NaCl concentration has no detectable influence on the results (FIG. 3 A/B, FIG. 5 A/B). No activity was detected with each of the methods employed in B/B serum deficient in MBL. On IgM coated plates only a very low activity was detected in both methods (FIG. 4A and B, FIG. 6A and B). Note different scales! At low NaCl concentration, the activity was slightly higher in both pro-urokinase and C4 methods. The background activity with MBL deficient B/B serum was hardly detectable.

These results indicate that pro-urokinase is hardly activated by the classic route of the complement system operational using IgM coating, whereas it is a good substrate for the MBL-MASP route detected using the mannan coated plates.

Example 5

Activity of Recombinant MASP-2 on Novel Substrates.

Figure 7:
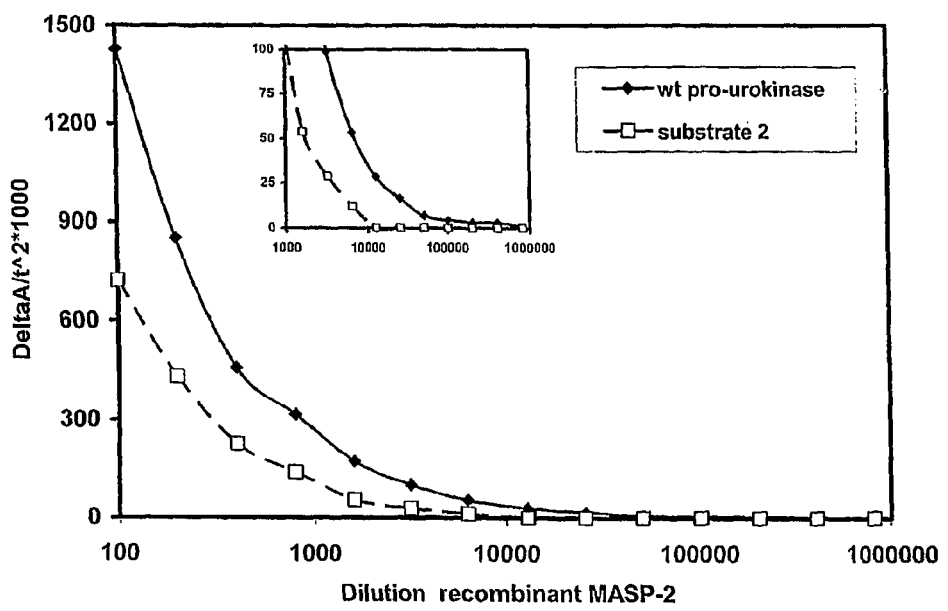

The activity of purified recombinant MASP-2 on wt pro-urokinase and substrate 2 was investigated. Recombinant MASP-2 (active form) at 600 µg/ml was serially diluted in 50 mM Tris HCl pH7.6, 1.5 mM NaCl, 0.5 mM $CaCl_2$, 1 µM $ZnCl_2$, 0.01% (v/v) BRIJ35™. To wells of a microtiter plate 100 µl of MASP-2 dilution, 10 µof wt pro-urokinase at approximately 50 µg/ml) or 10 µl substrate 2 (at approximately 75 µg/ml) were added, followed by 10 µl of peptide substrate pyro Glu-Gly-Arg-pNA (at 6 mM). The plate was incubated at 37° C. and absorbance change at 405 nm was followed in time for 2 h. The results are shown in FIG. 7. MASP-2 can be detected with both substrates, but activity with wt pro-urokinase is about 2 fold higher than with substrate 2.

Example 6

Effect of Mannan Coating Concentration on Capture Assay Response.

Figure 8:
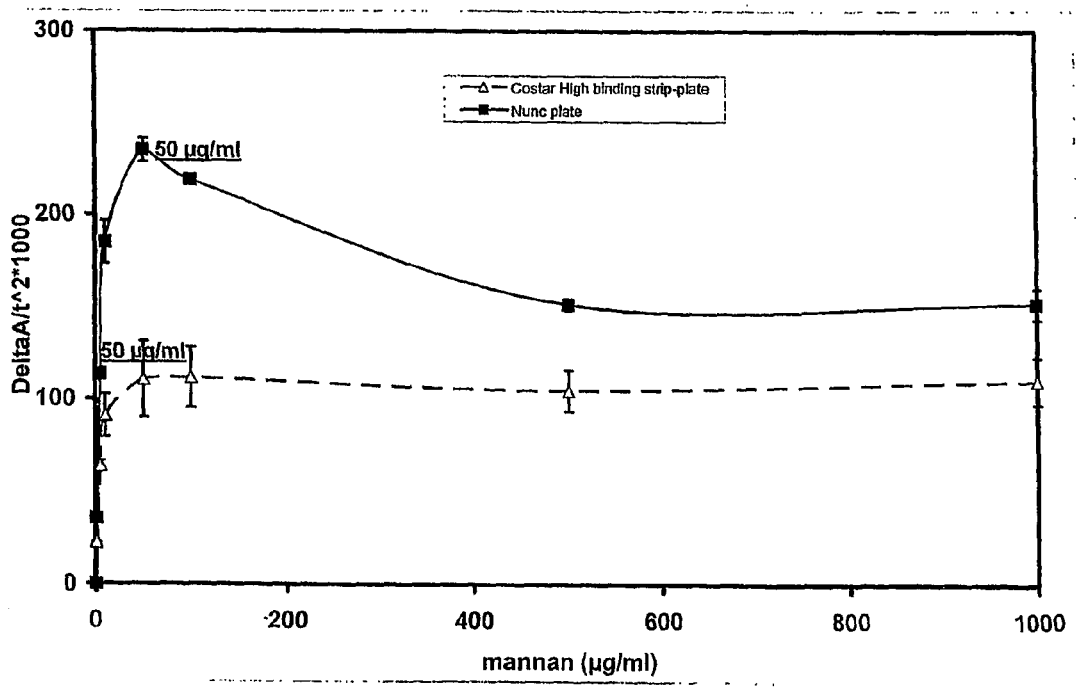

Wells of microtiter plates (either Nunc Maxisorb or Costar high binding) were filled with 100 μl of a solution of mannan (0-1000 μg/ml) in 0.1 M Na-Carbonate buffer pH 9.6 at 37° C. for 2 h. Subsequently, the plates were washed four times with 10 mM Na-phosphate pH 7.5, 0.15 M NaCl, 0.05% (v/v) Tween20™ (PBS/T) and blocked with 1% (w/v) bovine serum albumin in the same buffer. Human serum was diluted 40 fold in 10 mM barbital, 1.0 M NaCl, 0.1% (w/v) gelatin, 2 mM CaCl$_2$, 2 mM MgCl$_2$, 0.05% (v/v) Tween20™, pH7.3 (GVB++) and 100 μl of diluted serum was added to wells of the mannan coated microtiter plates. After 1 h incubation at 4° C., to enable binding of MBL-MASP complexes from the serum to the mannan coated wells, the wells were washed with PBS/T+5 mM CaCl$_2$ and subsequently 100 μl of 50 mM Tris HCl pH 7.6, 1.5 mM NaCl, 0.5 mM CaCl$_2$, 1 μM ZnCl$_2$, 0.01% (v/v) BRIJ35™ followed by 10 μl of wt pro-urokinase (at 50 μg/ml) and 10 μl pyro-Glu-Gly-Arg-pNA were added. The plate was shaken with a plateshaker and incubated for 2 h at 37° C. The absorbance change at 405 nm was measured at regular intervals with a microtiter plate reader. The activities were expressed as ($\Delta A/h^2 \times 1000$). The results are shown in FIG. 8. It is concluded that coating at a mannan concentration of 50 μg/ml is optimal with both types of plates. The Nunc plate shows an about 2 fold higher response at 50 μg/ml coating concentration as compared with the Costar plate. At higher coating concentrations the response of the Nunc plate drops to a slightly lower level, whereas the response with the Costar plate is very constant over a very broad concentration range.

Example 7

Effect of Inhibitor on Serum MASP Activity.

Figure 9:
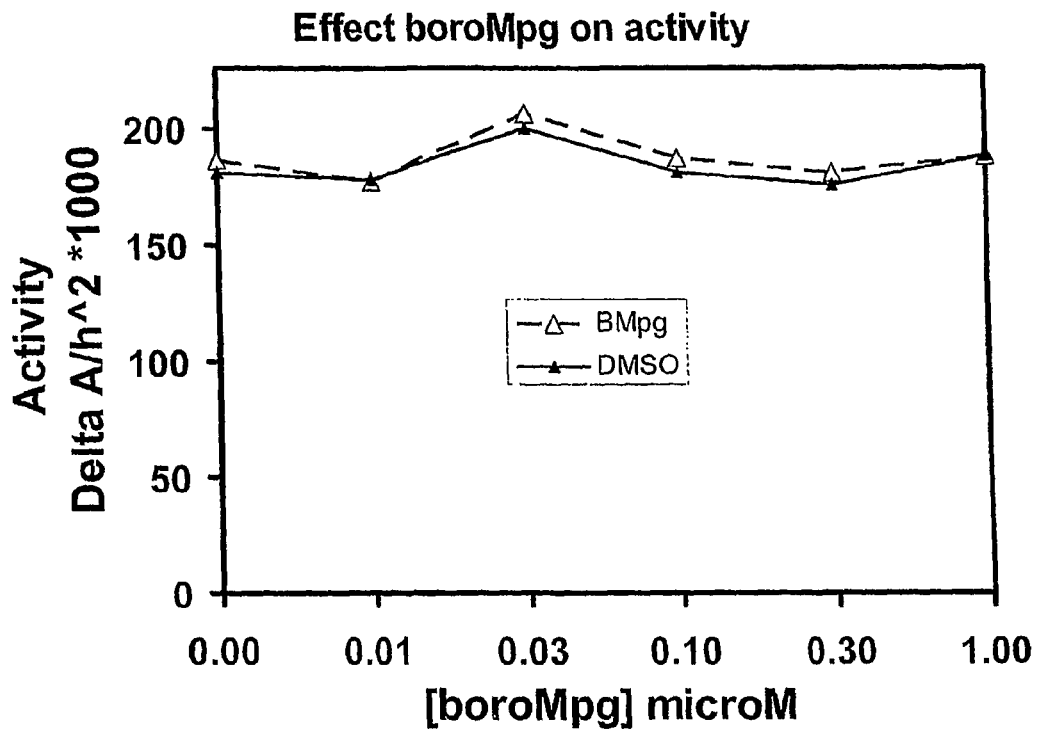

A mannan coated plate was used to capture MBL-MASP complex from diluted human serum. After washing, 100 μl buffer containing 0-1 μM Z-D-Phe-Pro-methoxypropylboroglycine-pinanediolester (BMpg or boroMpg) or buffer containing an identical volume of DMSO (solvent of boroMpg), 15 μl (50 μg/ml) wild-type pro-urokinase and 10 μl (6 mM) pyro-Glu-Gly-Arg-pNA were added. The plate was incubated at 37° C. and colour formation was followed for 2 h with a plate reader at 405 nm. Activities were expressed as $\Delta A/h^2 \times 1000$. All details are as described in Example 4. The results summarized in FIG. 9 show no effect of BMpg on activity of the captured MBL-MASP complex. Since BMpg is known to inhibit MASP-1 but not MASP-2, this could mean that the assay detects predominantly MBL-MASP-2 complexes and not MBL-MASP-1 complexes (ref Presanis et al. Mol. Immunol. 2003; 40:921-929)

Example 8

Effect of Buffer Composition on Performance of Serum MASP Activity Assay.

In this example the effect of the buffer composition on the performance of a MASP activity assay according to the invention was investigated. MBL-MASP complexes from wild-type (A/A) serum and deficient (B/B) serum diluted 50- or 100-fold in buffers of various compositions were captured on a mannan coated plate. Apart from the buffer composition, the procedure of Example 4 was followed. After capture, the plate was washed 4 times with 50 mM TrisHCl, 1.5 mM NaCl, 0.5 mM CaCl$_2$, 0.01% (v/v) BRIJ 35™, pH 8.0. After washing, 50 mM TrisHCl, 1.5 mM NaCl, 0.5 mM CaCl$_2$, 0.01% (v/v) BRIJ 35™, pH 8.0, pro-urokinase and peptide substrate were added and activity was measured. The sera were diluted in the following buffers: GVB++ 0.15 M NaCl; GVB++ 1 M NaCl; 50 mM TrisHCl, 75 mM NaCl with additions; 50 mM TrisHCl, 150 mM NaCl; 50 mM TrisHCl, 1 M NaCl; 50 mM TrisHCl; 200 mM TrisHCl; 400 mM TrisHCl. All Tris buffers were pH 8.0 and contained 0.5 mM CaCl$_2$ and 0.01% (v/v) BRIJ 35™.

Figure 10:
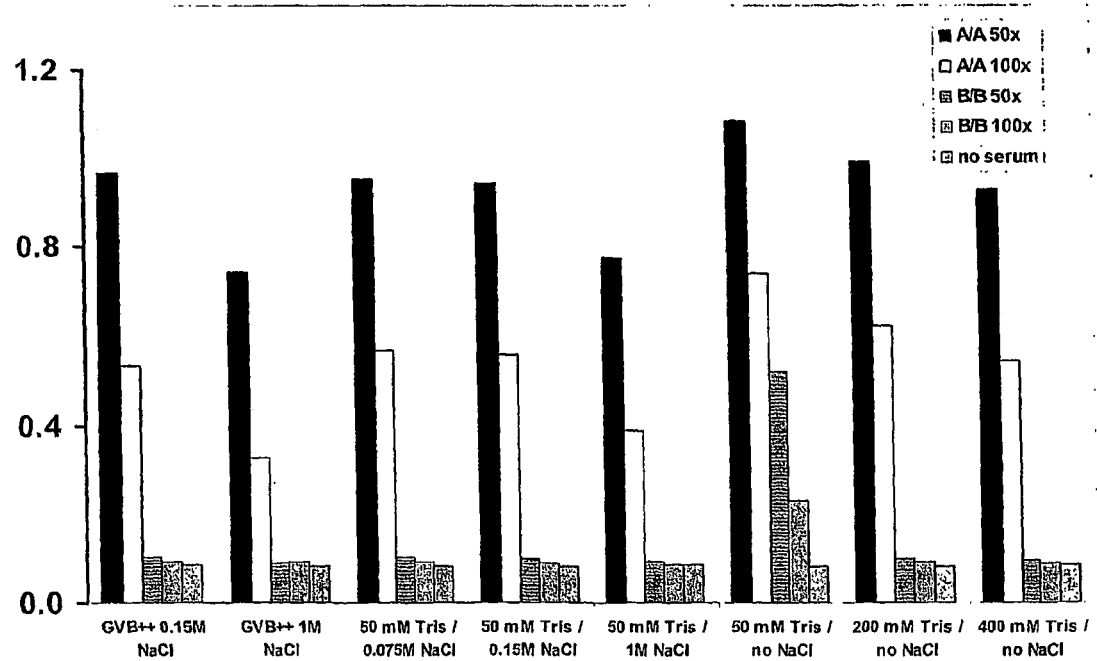

After capture of MBL-MASP from the sera diluted in the different buffers, the plates were emptied and washed with 50 mM Tris, 1.5 mM NaCl, 0.5 mM CaCl$_2$, 0.01% Brij35, pH 8.0. Subsequently pro-urokinase and pyro-Glu-Gly-Arg-pNA were added in the latter buffer and color formation was followed. All other details are as described in Example 4. The results are shown in FIG. 10. The buffer composition is not very critical. Only the buffer containing 50 mM TrisHCl without any added salt showed a high activity with the MBL deficient (B/B) serum, all other buffers deliver comparable results for all different sera. There is a slight trend for higher responses with lower salt concentrations.

Example 9

Cross Reactivity of Complement Components in MBL-MASP Assay.

Figure 11:
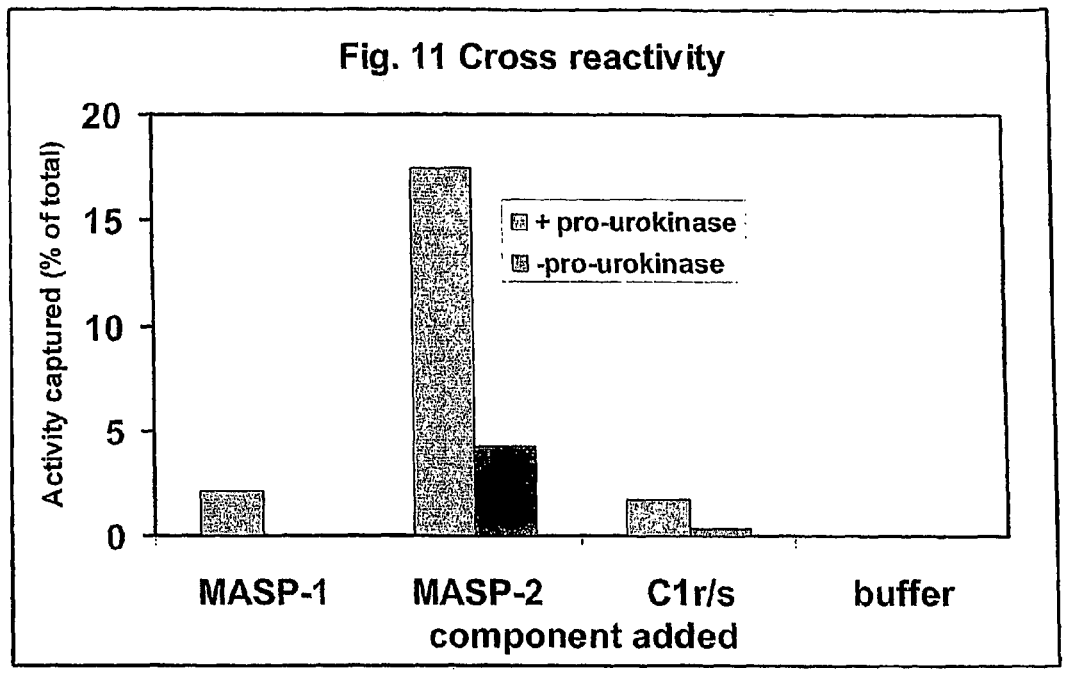

To mannan coated wells of a microtiterplate 100-fold diluted (A/B) serum in 50 mM Tris.HCl, 75 mM NaCl, 0.5 mM CaCl$_2$, 0.01% (v/v) Brij35™, pH 8.0 was added and incubated during 1 h at 4° C. After washing, purified recombinant MASP-1, MASP-2 and C1r/s in 50 mM Tris,75 mM NaCl, 0.5 mM CaCl$_2$,0.01% Brij35, pH 8.0 or only buffer as control were added and again incubated for 1 h at 4° C. The supernatant liquid was removed and brought in a new non-coated plate. The capture plate was washed and to both the capture plate and supernatant plate buffer with or without detection enzyme pro-urokinase and pyro-Glu-Gly-Arg-pNA were added as described before. The activities bound to the capture plate and in the supernatant were determined. The activity bound to the capture plate was expressed as percentage of total activity (bound to plate plus in supernatant). The result are shown in FIG. 11. There is a slight cross reactivity due to externally added MASP-1 or C1r/s. Externally added MASP-2 is still able to bind pointing to the presence of some free non-complexed MBL to the mannan coated plate. There is a slight activity directly on the peptide substrate.

Example 10

Determination of MBL-MASP Activity in Various Sera using the Pro-urokinase Based Assay and the Traditional C4 Activation Assay.

Figure 12:
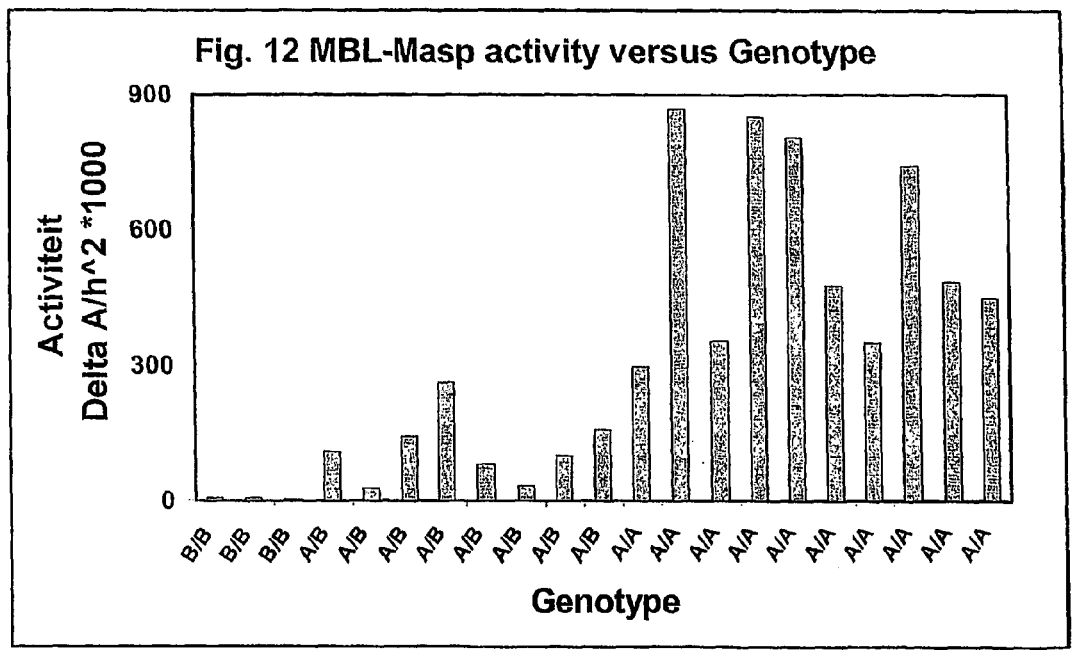
Figure 13:
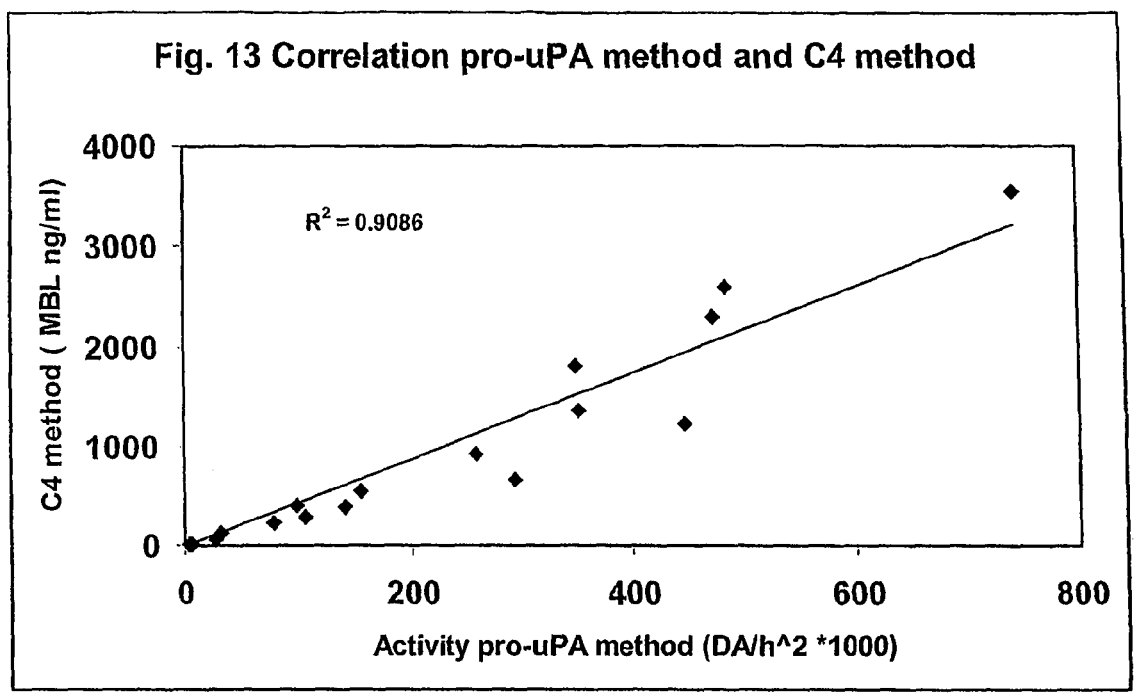

Twenty-one serum samples from individuals with known MBL genotype were analysed for MBL-MASP activity using the pro-urokinase method as described in Example 8, using the 50 mM TrisHCl pH 8.0, 75 mM NaCl, 0.5 mM CaCl$_2$ and 0.01% (v/v) BRIJ35™ buffer during capture. Activity was expressed as Delta $A^{405}/h^2 \times 1000$. The results are summarised in FIG. 12. The three genotypes, homozygous deficient (B/B), heterozygous deficient (A/B) and normals (A/A) can clearly be discerned. In the same sera the MBL-MASP levels were also measured using the traditional C4 method as described in Example 4. The results obtained with both methods show an very good correlation as shown in FIG. 13.

REFERENCES

Gadjera M, Thiel S, Jensenius J C. The mannan-binding-lectin pathway of the innate immune response. Curr Opin Immunol 2001; 13: 74-78.

Gadjeva M, Takahashi K, Thiel S. Mannan-binding lectin-a soluble pattern recognition molecule. Molec Immunol 2004; 41: 113-121.

Kasai S, Arimura H, Nishida M, Suyama T. Primary structure of single-chain pro-urokinase. J Biol Chem 1985; 260: 12382-12389

Matsushita M, Endo Y, Fujita T. Complement-activating complex of ficolin and mannose-binding lectin-associated serine protease. J Immunol 2000; 164: 2281-2284.

Moller-Kristensen M, Jensenius J C, Jensen L, Thielens N, Rossi V, Arlaud G, Thiel S. Levels of mannan-binding lectin associated serine protease-2 in healthy individuals. J Immunol Methods 2003; 282: 159-167.Presanis J S, Hajela K, Ambrus G, Gal P, Sim R B. Differential substrate and inhibitor profiles for human MASP-1 and MASP-2. Molec Immunol 2003; 40: 921-929.

Petersen S V, Thiel S, Jensen L, Steffensen R, Jensenius J C. An assay for the mannan-binding lectin pathway of complement activation. J Immunol Methods 2001; 257: 107-116.

Roos A, Bouwman L H, Munoz J, Zuiverloon T, Faber-Krol M C, Fallaux-van den Houten F C, Klar-Mohamad N, Hack C E, Tilanus M G, Daha M R. Functional characterization of the lectin pathway of complement in human serum. Mol Immunol 2003; 39:655-668.

Roos A, Garred P, Wildenberg M E, Lynch N J, Munoz R J, Zuiverloon T C, Bouwman L H, Schlagwein N, Fallaux-van Houten F C, Faber-Krol M C, Madsen H O, Schwaeble W J, Matsushita M, Fujita T, Daha M R. Antibody-mediated activation of the classical pathway of complement may compensate for mannose-binding lectin deficiency. Eur J Immunol. 2004; 34(9):2589-98.

Sim R B, Tsiftsoglou S A. Proteases of the complement system. Biochem Soc Trans 2004; 32: 21-27.

Stengaard-Pedersen K, Thiel S, Gadjeva M, Moller-Kristensen M, Sorensen R, Jensen L T, Sjoholm A G, Fugger L, Jensenius J C. Inherited deficiency of mannan-binding lectin-associated serine protease 2. N Engl J Med 2003; 349: 554-560.

Thiel S, Moller-Kristensen M, Jensen L, Jensenius J C. Assays for the functional activity of the mannan-binding lectin pathway of complement activation. Immunobiol 2002; 205:446-454.

Turner M W. The role of mannose-binding lectin in health and disease. Mol Immunol 2003; 40: 423-429.

The invention claimed is:

1. A method for determining the activity of a mannan-binding-lectin associated serine protease (MASP) in a sample, the method comprising the steps of:
incubating the sample with a pro-urokinase comprising at its activation site the consensus sequence Arg/Leu/Gly-Yyy-Arg/Lys-Ile/Leu/Val-Zzz-Gly-Gly (SEQ ID NO:1), wherein Yyy can be any amino acid and Zzz is an aliphatic amino acid;
measuring proteolytic activation of said pro-urokinase incubated with said sample; and
determining MASP activity in the sample based on said proteolytic activation.

2. A method according to claim 1, wherein said pro-urokinase comprises the sequence Arg-Phe-Lys-Ile-Ile-Gly-Gly (SEQ ID NO:27) at its activation site.

3. A method according to claim 1, wherein said pro-urokinase comprises a sequence at its activation site selected from the group consisting of the sequences Gly-Leu-Arg-Ile-Ile-Gly-Gly (SEQ ID NO:16); Leu-Thr-Arg-Ile-Val-Gly-Gly (SEQ ID NO:17); Leu-Gly-Arg-Ile-Ile-Gly-Gly (SEQ ID NO:28); Leu-Gly-Lys-Ile-Ile-Gly-Gly (SEQ ID NO:29); Leu-Gln-Arg-Ile-Ile-Gly-Gly (SEQ ID NO:20); Leu-Gln-Lys-Ile-Ile-Gly-Gly (SEQ ID NO:21;
Arg-Gln-Arg-Ile-Ile-Gly-Gly (SEQ ID NO:22) and Arg-Gln-Lys-Ile-Ile-Gly-Gly (SEQ ID NO:23).

4. A method for determining the activity of a mannan-binding-lectin associated serine protease (MASP) in a sample, the method comprising the steps of:
incubating a sample with a recombinant non-pro-urokinase pro-enzyme, wherein its activation site comprises the activation sequence Arg/Leu/Gly-Yyy-Arg/Lys, Yyy being any amino acid;
measuring proteolytic activation of said pro-enzyme incubated with said sample; and
determining MASP activity in the sample based on said proteolytic activation.

5. A method according to claim 4, wherein said non-urokinase pro-enzyme comprises at its activation site the activation sequence Arg-Phe-Lys.

6. A method according to claim 5, wherein said non-urokinase pro-enzyme is selected from the group consisting of the pro-enzymes of serine proteases, with the exception of pro-urokinase cysteine proteases, aspartic proteases and metallo-proteases.

7. A method according to claim 6, wherein said pro-enzyme is a pro-caspase and wherein said activation sequence is positioned within a distance of up to 30 amino acid residues from the natural activation sequence of said pro-caspase.

8. A method according to claim 1, wherein said MASP is present in a complex with a lectin.

9. A method according to claim 1, wherein said MASP is selected from the group consisting of MASP-1, MASP-2 and MASP-3.

10. A method according to claim 1, wherein determining the proteolytic cleavage of said pro-urokinase comprises the use of a peptide substrate which releases a detectable label upon hydrolysis by the activated enzyme.

11. A method according to claim 10, wherein the proteolytic activation of pro-urokinase is performed using as a peptide substrate the compound Xxx-Yyy-Arg-pNA, Xxx and Yyy being any amino acid and pNA representing a para-nitroaniline moiety.

12. A method according to claim 10, wherein the proteolytic activation of pro-urokinase is performed using plasminogen as a substrate and wherein plasminogen cleavage by urokinase is determined using a plasmin-specific peptide substrate which releases a coloured or fluorescent group upon hydrolysis by plasmin.

13. A method according to claim 1, comprising immobilizing MASP or a MASP/lectin complex on a solid surface using a specific binding molecule of MASP or the MASP/lectin complex.

14. A method according to claim 13, wherein said specific binding molecule is an antibody or fragment thereof or a carbohydrate.

15. A method for the detection of a mannan-binding lectin, comprising the steps of:
    adding to a solution suspected of comprising a mannan-binding lectin an amount of mannan-binding-lectin associated serine protease (MASP);
    incubating the solution and MASP with a pro-urokinase comprising at its activation site the consensus sequence Arg/Leu/Gly-Yyy-Arg/Lys-Ile/Leu/Val-Zzz-Gly-Gly (SEQ ID NO:1), wherein Yyy can be any amino acid and Zzz is an aliphatic amino acid;
    measuring proteolytic activation of said pro-urokinase incubated with said solution and MASP; and
    determining MASP activity in the solution, whereby the presence of MASP activity indicates the presence of mannan-binding lectin in the sample.

16. A method of using a pro-urokinase as reporter enzyme in a functional MASP assay, the method comprising the steps of:
    incubating a sample with a pro-urokinase comprising at its activation site the consensus sequence Arg/Leu/Gly-Yyy-Arg/Lys-Ile/Leu/Val-Zzz-Gly-Gly (SEQ ID NO:1), wherein Yyy can be any amino acid and Zzz is an aliphatic amino acid;
    measuring proteolytic activation of said pro-urokinase incubated with said sample; and
    determining MASP activity in the sample based on said proteolytic activation.

17. A method according to claim 4, wherein said MASP is present in a complex with a lectin.

18. A method according to claim 1, wherein:
    said MASP is present in a complex with a lectin;
    said MASP is selected from the group consisting of MASP-1, MASP-2 and MASP-3;
    determining the proteolytic cleavage of said pro-urokinase pro-enzyme comprises the use of a peptide substrate which releases a detectable label upon hydrolysis by the activated enzyme;
    the proteolytic activation of said pro-urokinase is determined either by using a peptide substrate comprising the compound Xxx-Yyy-Arg-pNA, Xxx and Yyy being any amino acid and pNA representing a para-nitroaniline moiety, or by using plasminogen as a substrate and wherein plasminogen cleavage by urokinase is determined using a plasmin-specific peptide substrate which releases a coloured or fluorescent group upon hydrolysis by plasmin;
    said MASP or said MASP/lectin complex is immobilized on a solid surface using a specific binding molecule of said MASP or said MASP/lectin complex;
    said specific binding molecule is an antibody or fragment thereof or a carbohydrate.

19. A method for the detection of a mannan-binding lectin, the method comprising the steps of:
    adding to a solution suspected of comprising a mannan-binding lectin an amount of mannan-binding-lectin associated serine protease (MASP);
    incubating the solution and MASP with a recombinant non-pro-urokinase pro-enzyme, wherein its activation site comprises the activation sequence Arg/Leu/Gly-Yyy-Arg/Lys, Yyy being any amino acid;
    measuring proteolytic activation of said pro-enzyme incubated with said solution and MASP; and
    determining MASP activity in the solution, whereby the presence of MASP activity indicates the presence of mannan-binding lectin in the sample.

20. The method according to claim 19, wherein:
    said non-pro-urokinase pro-enzyme comprises at its activation site the activation sequence Arg-Phe-Lys;
    said non-pro-urokinase pro-enzyme is selected from the group consisting of the pro-enzymes of serine proteases, with the exception of pro-urokinase, cysteine proteases, aspartic proteases and metalloproteases;
    said MASP is present in a complex with a lectin;
    said MASP is selected from the group consisting of MASP-1, MASP-2 and MASP-3;
    determining the proteolytic cleavage of said non-pro-urokinase pro-enzyme comprises the use of a peptide substrate which releases a detectable label upon hydrolysis by the activated enzyme;
    said MASP or said MASP/lectin complex is immobilized on a solid surface using a specific binding molecule of said MASP or said MASP/lectin complex;
    said specific binding molecule is an antibody or fragment thereof or a carbohydrate.

21. The method according to claim 19, wherein said pro-enzyme is a pro-caspase and wherein said activation sequence is positioned within a distance of up to 30 amino acid residues from the natural activation sequence of said pro-caspase.

* * * * *

UNITED STATES PATENT AND TRADEMARK OFFICE
CERTIFICATE OF CORRECTION

PATENT NO. : 7,811,771 B2  
APPLICATION NO. : 11/793851  
DATED : October 12, 2010  
INVENTOR(S) : Verheijen et al.

Page 1 of 1

It is certified that error appears in the above-identified patent and that said Letters Patent is hereby corrected as shown below:

In the Specification

Column 1, line 53, "ot" should read --of--;

Column 2, line 41, "pro-uroidnase" should read --pro-urokinase--;

Column 7, line 6, "thereof" should read --thereof)--;

Column 14, line 20, "C1 $_r$ and C1 $_s$" should read --C1$_r$ and C1$_s$--;

Column 14, line 22, "C1 $_r$ and C1 $_s$" should read --C1$_r$ and C1$_s$--;

Column 14, line 24, "C1 $_r$ and C1 $_s$" should read --C1$_r$ and C1$_s$--; and Column 14, line 59, "10 μof" should read --10 μl of--.

Signed and Sealed this  
Twenty-sixth Day of November, 2013

Margaret A. Focarino  
*Commissioner for Patents of the United States Patent and Trademark Office*